United States Patent
Fallon (10) Patent No.: US 8,012,710 B2
(45) Date of Patent: *Sep. 6, 2011

(54) METHODS OF TREATING AND DIAGNOSING PARKINSONS DISEASE AND RELATED DYSAUTONOMIC DISORDERS

(75) Inventor: Joan M. Fallon, Bronxville, NY (US)

(73) Assignee: Curemark, LLC, Rye, NY (US)

(*) Notice: Subject to any disclaimer, the term of this patent is extended or adjusted under 35 U.S.C. 154(b) by 0 days.

This patent is subject to a terminal disclaimer.

(21) Appl. No.: 12/487,868

(22) Filed: Jun. 19, 2009

(65) Prior Publication Data

US 2009/0285790 A1    Nov. 19, 2009

Related U.S. Application Data

(60) Continuation of application No. 12/046,252, filed on Mar. 11, 2008, which is a division of application No. 11/555,697, filed on Nov. 2, 2006, which is a continuation-in-part of application No. 10/730,567, filed on Dec. 8, 2003, now Pat. No. 7,138,123, which is a continuation of application No. 09/929,592, filed on Aug. 14, 2001, now Pat. No. 6,660,831.

(60) Provisional application No. 60/224,991, filed on Aug. 14, 2000.

(51) Int. Cl.
*C12Q 1/37* (2006.01)
*C07K 7/00* (2006.01)

(52) U.S. Cl. .................... 435/23; 530/309

(58) Field of Classification Search .................. None
See application file for complete search history.

(56) References Cited

U.S. PATENT DOCUMENTS

| | | | |
|---|---|---|---|
| 3,002,883 A | 10/1961 | Butt et al. | |
| 3,223,594 A | 12/1965 | Hoek et al. | |
| 3,357,894 A | 12/1967 | Jose et al. | |
| 3,515,642 A | 6/1970 | Mima et al. | |
| 3,574,819 A | 4/1971 | Gross et al. | |
| 3,940,478 A | 2/1976 | Kurtz | |
| 4,079,125 A | 3/1978 | Sipos | |
| 4,145,410 A | 3/1979 | Sears | |
| 4,241,046 A | 12/1980 | Papahadjopoulos et al. | |
| 4,826,679 A | 5/1989 | Roy | |
| 5,190,775 A | 3/1993 | Klose | |
| 5,250,418 A | 10/1993 | Moller et al. | |
| 5,324,514 A | 6/1994 | Sipos | |
| 5,436,319 A | 7/1995 | Kung et al. | |
| 5,437,319 A | 8/1995 | Garuglieri | |
| 5,439,935 A | 8/1995 | Rawlings et al. | |
| 5,460,812 A | 10/1995 | Sipos | |
| 5,476,661 A | 12/1995 | Pillai et al. | |
| 5,527,678 A | 6/1996 | Blaser et al. | |
| 5,585,115 A | 12/1996 | Sherwood et al. | |
| 5,607,863 A | 3/1997 | Chandler | |
| 5,648,335 A | 7/1997 | Lewis et al. | |
| 5,674,532 A | 10/1997 | Atzl et al. | |
| 5,686,311 A | 11/1997 | Shaw | |
| 5,750,104 A | 5/1998 | Sipos | |
| 5,776,917 A | 7/1998 | Blank et al. | |
| 5,858,758 A | 1/1999 | Hillman et al. | |
| 5,952,178 A | 9/1999 | Lapidus et al. | |
| 5,958,875 A | 9/1999 | Longo et al. | |
| 5,985,891 A | 11/1999 | Rowe | |
| 6,011,001 A | 1/2000 | Navia et al. | |
| 6,013,286 A | 1/2000 | Klose | |
| 6,020,310 A | 2/2000 | Beck et al. | |
| 6,020,314 A | 2/2000 | McMichael | |
| 6,153,236 A | 11/2000 | Wu et al. | |
| 6,187,309 B1 | 2/2001 | McMichael et al. | |
| 6,197,746 B1 | 3/2001 | Beck et al. | |
| 6,210,950 B1 | 4/2001 | Johnson et al. | |
| 6,251,478 B1 | 6/2001 | Pacifico et al. | |
| 6,261,613 B1 | 7/2001 | Narayanaswamy et al. | |
| 6,280,726 B1 | 8/2001 | Weinrauch et al. | |
| 6,309,669 B1 | 10/2001 | Setterstrom et al. | |
| 6,399,101 B1 | 6/2002 | Frontanes et al. | |
| 6,482,839 B1 | 11/2002 | Thornfeldt | |
| 6,534,063 B1 | 3/2003 | Fallon | |
| 6,534,259 B1 | 3/2003 | Wakefield | |
| 6,632,429 B1 | 10/2003 | Fallon | |
| 6,660,831 B2 | 12/2003 | Fallon | |
| 6,727,073 B1 | 4/2004 | Moore et al. | |
| 6,743,447 B2 | 6/2004 | Labergerie et al. | |

(Continued)

FOREIGN PATENT DOCUMENTS

DE    43 32 985    3/1995

(Continued)

OTHER PUBLICATIONS

"Correlation between protein intake and daily levodopa dosage," Azilect/Rasagiline, Obtained from the Internet May 2, 2007, http://www.azilect.eu/media/cnsnews/showitem.aspx?i=d1c603e4-3c61-4aa1-a376-6e519a5a0f80, anonymous, (2006).

(Continued)

*Primary Examiner* — Rebecca Prouty
*Assistant Examiner* — Paul Martin
(74) *Attorney, Agent, or Firm* — Wilson Sonsini Goodrich & Rosati (57) ABSTRACT

A method for treating a Parkinson's patient with digestive/pancreatic enzymes involves administering an effective amount of digestive/pancreatic enzymes to an individual having the disorder in order to improve a symptom of the disorder. In addition, a method is provided for determining whether an individual has, or may develop, Parkinson's disease or related dysautonomic disorders and for determining whether an individual will benefit from the administration of pancreatic/digestive enzymes to treat the dysautonomic disorder.

41 Claims, 6 Drawing Sheets

U.S. PATENT DOCUMENTS

| | | |
|---|---|---|
| 6,797,291 B2 | 9/2004 | Richardson |
| 6,835,397 B2 | 12/2004 | Lee et al. |
| 6,852,487 B1 | 2/2005 | Barany et al. |
| 7,101,573 B2 | 9/2006 | Szymczak et al. |
| 7,129,053 B1 | 10/2006 | Reiter et al. |
| 7,138,123 B2 | 11/2006 | Fallon |
| 2002/0037284 A1 | 3/2002 | Fallon |
| 2002/0081628 A1 | 6/2002 | Fallon |
| 2002/0090653 A1 | 7/2002 | Fallon |
| 2003/0097122 A1 | 5/2003 | Ganz et al. |
| 2004/0057944 A1 | 3/2004 | Galle et al. |
| 2004/0057962 A1 | 3/2004 | Timmerman |
| 2004/0071683 A1 | 4/2004 | Fallon |
| 2004/0076590 A1 | 4/2004 | Wilkins |
| 2004/0101562 A1 | 5/2004 | Maio |
| 2004/0121002 A1 | 6/2004 | Lee et al. |
| 2004/0209790 A1 | 10/2004 | Sava et al. |
| 2005/0187130 A1 | 8/2005 | Brooker et al. |
| 2006/0105379 A1 | 5/2006 | Wu et al. |
| 2006/0182728 A1 | 8/2006 | Fallon |
| 2006/0183180 A1 | 8/2006 | Fallon |
| 2006/0198838 A1 | 9/2006 | Fallon |
| 2006/0259995 A1 | 11/2006 | Cayouette et al. |
| 2007/0053895 A1 | 3/2007 | Fallon |
| 2007/0116695 A1 | 5/2007 | Fallon |
| 2008/0058282 A1 | 3/2008 | Fallon |
| 2008/0152637 A1 | 6/2008 | Fallon |
| 2008/0161265 A1 | 7/2008 | Fallon et al. |
| 2008/0166334 A1 | 7/2008 | Fallon |
| 2008/0219966 A1 | 9/2008 | Fallon |
| 2008/0254009 A1 | 10/2008 | Finegold |
| 2008/0279839 A1 | 11/2008 | Schuler et al. |
| 2008/0317731 A1 | 12/2008 | Gramatikova et al. |
| 2009/0130081 A1 | 5/2009 | Fallon |
| 2009/0197289 A1 | 8/2009 | Fallon |
| 2009/0232789 A1 | 9/2009 | Fallon |
| 2009/0263372 A1 | 10/2009 | Fallon |
| 2009/0286270 A1 | 11/2009 | Fallon |
| 2009/0324572 A1 | 12/2009 | Fallon |
| 2009/0324730 A1 | 12/2009 | Fallon |
| 2010/0092447 A1 | 4/2010 | Fallon |
| 2010/0169409 A1 | 7/2010 | Fallon et al. |
| 2010/0233218 A1 | 9/2010 | Fallon |
| 2010/0260857 A1 | 10/2010 | Fallon et al. |

FOREIGN PATENT DOCUMENTS

| | | |
|---|---|---|
| EP | 0451484 A1 | 10/1991 |
| EP | 0564739 A3 | 4/1995 |
| EP | 0 564 739 | 1/2000 |
| GB | 2347742 A | 9/2000 |
| JP | 62230714 A | 10/1987 |
| WO | WO 95/22344 | 8/1995 |
| WO | WO 98/22499 | 5/1998 |
| WO | WO 98/52593 | 11/1998 |
| WO | WO 99/64059 | 12/1999 |
| WO | WO 00/09142 | 2/2000 |
| WO | WO 01/27612 A2 | 4/2001 |
| WO | WO 01/43764 | 6/2001 |
| WO | WO 01/27612 A3 | 10/2001 |
| WO | WO 02/14537 A2 | 2/2002 |
| WO | WO 02/14537 A3 | 5/2002 |
| WO | WO 2009/114757 A2 | 9/2009 |
| WO | WO 2010/002972 A1 | 1/2010 |
| WO | WO 2010/080830 A1 | 7/2010 |
| WO | WO 2010/080835 A1 | 7/2010 |

OTHER PUBLICATIONS

"Digestive Enzyme," Retrieved from the internet.<http://en.wikipedia.org/wiki/Digestive_enzyme>. Retrieved on Sep. 10, 2009.

"NINDS Dysautonimia Information Page," Retrieved from the internet on Sep. 10, 2009. http://www.ninds.nih.gov/disorders/dysautonomia/dysautonomia.htm, anonymous.

"NINDS Guillain-Barre Syndrome Information Page," Retrieved from the internet on Sep. 15, 2009, http://www.ninds.nih.gov/disorders/gbs/gbs.htm, anonymous.

Adams, "Summary of Defeat Autism Now! (DNN!) Oct. 2001 Converence," Retrieved from the Internet Dec. 18, 2008, http://puterakembara.org/rm/DAN2001.htm.

Axelrod, "Secretin Treatment for Gastrointestinal Dysmobility in Patients with Familial Dysautonomia," New York University School of Medicine, Grant Recipient Awards, Mar.-May 2000, www.med.nyu.edu/ogars/awards/awards 2000/page2.html.

Barlow, "A Comparison of the Blood Pressure, Kidney Volume and Pancreatic Secretory Response Following the Vein Administration of Various Secretin Preparations," *American Journ. of Phys.*, 1927, 81:182-188.

Belmonte and Bourgeron, "Fragile X syndrome and autism at the intersection of genetic and neural networks," *Nat. Neurosci.Neurosci*, Oct. 9, 2006, (10):1221-1225.

Blackmer, "Parkinson Disease: treatment and Medication," Mar. 10, 2009, Retrieved from the internet.<http://emedicine.medscape.com/article/312519-treatment>. Retrieved on Sep. 15, 2009.

Bode and Bode, "Usefulness of a simple photometric determination of chymotrypsin activity in stools—results of a multicentre study," *Clin Biochem.*, 1986, 19:333-337.

Campbell et al., "A genetic variant that disrupts *MET* transcription is associated with autism," *PNAS*, Nov. 7, 2006, 103(45):16834-16839.

Carlton, "Autism and Malnutrition: The Milk Connection," Retrieved from the Internet Feb. 18, 2008, http://www.mercola.com/2004/autism_malnutirition.htm.

Darman, "An introduction to Alternative Medicine for Psychiactric Conditions," [online] Oct. 22, 2007, [retrieved on Sep. 18, 2009] retrieved from: http:web.archive.org/web/20071022104238/http://altp[therapies4bipolar.info/ortho/html.

Dobbs et al., "Link between Helicobacter pylori infection and idiopathic Parkinsonism," *Medical Hypothesis*, 2000, 55(2):93-98.

Dockter et al., "Determination of chymotrypsin in the feces by a new photometric method," *Padiatr. Padol.*, 1985, 20(3):257-265, abstract only.

Finegold et al., "Gastrointestinal Microflora Studies in Late-Onset Autism," *Clinical Infectious Diseases*, 2002, 35(1):S6-S15.

Happe et al., "Time to give up on a single explanation for autism," *Nat. Neurosci.*, Oct. 9, 2006(10):1218-1220.

Horvath et al., "Improved Social and Language Skills After Secretion Administration in Patients with Autistic Spectrum Disorders," *Journal of the Association for Academic Minority Physicians*, Jan. 9, 1998, (1):9-15.

Hoshiko et al., "The Effect of the Gastrointestinal Hormones on Colonic Mucosal Blood Flow," *Acta Medica Nagasakiensia*, 1994, 39(4):125-130.

Kaspar et al., "New Photometric Assay for Chymotrypsin in Stool," *Clinical Chemistry*, 1984, 30(11):1753-1757.

Koster et al., "Evidence based medicine and extradigestive manifestations of *Helocobacter pylori*," *Acta Gastro-Enterologica Belgica*, 2000, 63(4):388-392.

Layer et al., "Pancreatin Enzyme Replacement Therapy," *Current Gastroenterology Reports*, 2001, 3:101-108.

MacReady, "Parkinson's Disease Treatment: What You Should Know," Retrieved from the internet. <http://www.everydayhealth.com/parkinsons-disease/parkinsons-disease-treatment-overview.aspx>. Retrieved on Sep. 15, 2009.

Marczewska et al., "Protein intake in Parkinsonian patients using the EPIC food frequency questionnaire," *Mov Disord.*, Aug. 21, 2006(8):1229-1231.

Marlicz and Chrzanowska, "Determination of Chymotrypsin in the Stool in the diagnosis of Chronic Pancreatitis," 1988, *Wiadomosci lekarskie*, 41(11):704-707, summary only.

"Autism," Merck Manual Online Medical Library Home Addition retrieved from the Internet Mar. 10, 2008, retrieved from http://www.merck.com/mmhge/sec23/ch286/ch286b.html.

Marsh, "Neuropsychiatric Aspects of Parkinson's Disease," *Psychosomatics*, Jan.-Feb. 2000, 41(1):15-23.

mayoclinic.com, "Autism," Retrieved from Internet Mar. 10, 2008, retrieved from http://www/mayoclinic.com/health/autism/DS00348/DSECTION=2.

Mayo Clinic Staff, "Bipolar disorder," [online], Jan. 4, 2008 [retrieved on Sep. 9, 2009], retrieved from: http://www.mayoclinic.com/health/bipolardisorder/DS00356/DSECTION=symptoms.

Mayo Clinic Staff, "Obsessive-compulsive disorder," [online] Dec. 21, 2006 [retrieved on Sep. 18, 2009] retrieved from http://www.preferredalternatives.org/lat/WellnessLibrary/anxiety&PanicDisorders/Obsessive-CompulsiveDisorder/Obsessive-CompulsiveDisorder-Mayoclinic.pdf.

Mayo Clinic Staff, "Opositional defiant disorder," [online] Dec. 19, 2007 [retrieved on Sep. 18, 2009], retrieved from: http://www.mayoclinic.com/health/oppositional-defiant-disorder/DS00630/DSECTION=symptoms.

Medsafe, Data Sheet for alpha-lactose, Jul. 21, 1999, retrieved from Internet Feb. 28, 2008, retrieved from http://www.medsafe.govt.nz/Profs/Datasheet/a/Alphalactulosesyrup.htm.

MeSH Browser, "Child Development Behavior Disorders, Pervasive," and "Attention Deficit and Disruptive Behavior Disorders," http://www.nlm.nih.gov/mesh/2002/MBrowser.html, National Library of Medicine, 2001.

Michell et al., "Biomarkers and Parkinson's Disease," *Brain*, Aug. 21, 2004, 127(8):1693-1705.

Nachaegari and Bansal, "Coprocessed excipients for solid dosage forms," Pharmaceutical Technology, Jan. 2004, pp. 52, 54, 56, 58, 60, 62, 64.

Parisi et al., "Evaluation of New Rapid Commercial Enzyme Immunoassay for Detection of Cryptosporidium Oocysts in Untreated Stool Specimens," J. Clin Microbiol., 1995, 33(7):1963-1965.

Remtulla et al., "Stool Chymotrypsin Activity Measured by a Spectrophotometric Procedure to Identify Pancreatic Disease in Infants," *Clinical Biochemistry*, Dec. 1986, 19:341-342.

Rogers, *No more heartburn: Stop the pain in 30 day—Naturally*, 2000, p. 172.

Schiller, "Review Articile: the therapy of constipation," *Aliment Pharmacol Ther.*, 2001, 15:749-763.

Sherwood and Becker, "A new class of high-functionality excipients: Silicified microcrystalline cellulose," *Pharm. Tech.*, Oct. 1998, 22 (10): 78-88.

Seneca and Henderson, "Enhancement Of Brain L-Dopa Concentration With A-Chymotrypsin," Journal of the American Geriatrics Society, 1973, pp. 256-258.

The Alzheimer's Association, "Basics of Alzheimer's Disease" [online], 2005 [retrieved on Sep. 18, 2009], retrieved from: http://www.alz.org/national/documents/brochure_basicsofalz_low/pdf.

Tsang et al., Extragastroduodenal conditions associated with *Helicpbacter pylori* infection, Hong Kong Medical Journal, 1999, 5(2):169-174.

Woodward et al., "Ischaemic enterocolitis complicating idiopathic dysatuonomia," *Gut*, 1998, 43:285-287.

USPTO Office Action in U.S. Appl. No. 10/681,018, mailed Jan. 8, 2010, 21 pages.

Kristina M. Grasso, Esq. PLLC Amendment in Reply to Action dated Aug. 18, 2008 in U.S. Appl. No. 10/681,018, filed Feb. 7, 2009, 7 pages.

USPTO Office Action in U.S. Appl. No. 10/681,018, mailed Aug. 18, 2008, 6 pages.

Kristina M. Grasso, Esq. PLLC Response to Advisory Action dated Jun. 3, 2008 in U.S. Appl. No. 10/681,018, filed Jun. 17, 2008, 11 pages.

USPTO Advisory Action in U.S. Appl. No. 10/681,018, mailed Jun. 3, 2008, 4 pages.

Kristina M. Grasso, Esq. PLLC Amendment in Reply to Action dated Mar. 17, 2008 in U.S. Appl. No. 10/681,018, filed May 19, 2008, 10 pages.

USPTO Final Office Action in U.S. Appl. No. 10/681,018, mailed Mar. 17, 2008, 10 pages.

Kristina M. Grasso, Esq. PLLC Amendment in Reply to Action dated Aug. 7, 2007 in U.S. Appl. No. 10/681,018, filed Dec. 7, 2007, 11 pages.

USPTO Office Action in U.S. Appl. No. 10/681,018, mailed Aug. 7, 2007, 10 pages.

Maine & Asmus Amendment in Reply to Action dated Dec. 22, 2006 in U.S. Appl. No. 10/681,018, filed May 18, 2007, 11 pages.

USPTO Office Action in U.S. Appl. No. 10/681,018, mailed Dec. 22, 2006, 8 pages.

Maine & Asmus Response to Election/Restriction Requirement dated Sep. 12, 2006 in U.S. Appl. No. 10/681,018, filed Oct. 3, 2006, 6 pages.

USPTO Office Action in U.S. Appl. No. 11/555,697, mailed Aug. 3, 2009, 11 pages.

Kristina M. Grasso, Esq. PLLC Amendment in Reply to Feb. 27, 2009 Final Office Action in U.S. Appl. No. 11/555,697, filed May 27, 2009, 12 pages.

USPTO Final Office Action in U.S. Appl. No. 11/555,697, mailed Feb. 27, 2009, 13 pages.

Kristina M. Grasso, Esq. PLLC Amendment in Reply to Sep. 25, 2008 Notice of Non-Responsive Amendment in U.S. Appl. No. 11/555,697, filed Oct. 24, 2008, 7 pages.

USPTO Notice of Non-Responsive Amendment in U.S. Appl. No. 11/555,697, mailed Sep. 25, 2008, 2 pages.

Kristina M. Grasso, Esq. PLLC Amendment in Reply to Mar. 28, 2008 Office Action in U.S. Appl. No. 11/555,697, filed Aug. 28, 2008, 10 pages.

USPTO Office Action in U.S. Appl. No. 11/555,697, mailed Mar. 28, 2008, 9 pages.

Kristina M. Grasso, Esq. PLLC Amendment in Reply to Feb. 11, 2008 Notice of Non-Responsive Amendment in U.S. Appl. No. 11/555,697, filed Feb. 29, 2008, 4 pages.

USPTO Notice of Non-Responsive Amendment in U.S. Appl. No. 11/555,697, mailed Feb. 11, 2008, 2 pages.

Kristina M. Grasso, Esq. PLLC Amendment in Reply to Oct. 17, 2007 Restriction Requirement in U.S. Appl. No. 11/555,697, filed Nov. 17, 2007, 6 pages.

USPTO Restriction Requirement in U.S. Appl. No. 11/555,697, mailed Oct. 17, 2007, 9 pages.

USPTO Office Action in U.S. Appl. No. 12/046,252, mailed Sep. 24, 2009, 11 pages.

Kristina M. Grasso, Esq. PLLC Amendment in Reply to Notice Non-Compliant Amendment dated Aug. 19, 2009 in U.S. Appl. No. 11/232,180, filed Aug. 19, 2009, 7 pages.

USPTO Notice Non-Compliant Amendment in U.S. Appl. No. 11/232,180, mailed Jun. 19, 2009, 2 pages.

Kristina M. Grasso, Esq. PLLC Amendment in Reply to Mar. 13, 2009 Final Office Action in U.S. Appl. No. 11/232,180, filed Jun. 15, 2009, 12 pages.

USPTO Final Office Action in U.S. Appl. No. 11/232,180, mailed Mar. 13, 2009, 13 pages.

Axcan Pharma Inc. Cdn Prescribing Information on VIOKASE Pancrelipase, USP tablets, powder. 2000: 1-3.

Heijerman, et al. Omeprazole enhances the efficacy of pancreatin (pancrease) in cystic fibrosis. Ann Intern Med. Feb. 1, 1991;114(3):200-1.

Kachrimanis, et al. Tensile strength and disintegration of tableted silicified microcrystalline cellulose: influences of interparticle bonding. J Pharm Sci. Jul. 2003;92(7):1489-501.

Mitchell, et al. Comparative trial of viokase, pancreatin and Pancrease pancrelipase (enteric coated beads) in the treatment of malabsorption in cystic fibrosis. Aust Paediatr J. Jun. 1982;18(2):114-7.

Office Action dated Mar. 29, 2011 for U.S. Appl. No. 12/054,343.

Office Action dated Mar. 30, 2011 for U.S. Appl. No. 12/786,739.

U.S. Appl. No. 13/002,136, filed Dec. 30, 2010, Fallon.

Advisory Action dated Jun. 3, 2008 for U.S. Appl. No. 10/681,018.

Amendment and Response dated Apr. 7, 2010 in Reply to Restriction Requirement dated Oct. 7, 2009 for U.S. Appl. No. 12/283,090.

Amendment dated Oct. 20, 2008 in Reply to Notice Non-responsive Amendment dated Sep. 22, 2008 for U.S. Appl. No. 11/232,180.

Amendment dated Nov. 13, 2009 in Reply to Final Office Action dated Jul. 27, 2004 for U.S. Appl. No. 09/990,909.

Amendment dated Dec. 12, 2007 in Reply to Office Action dated Aug. 8, 2007 for U.S. Appl. No. 11/213,382.

Amendment dated Dec. 7, 2007 in Reply to Office Action dated Aug. 7, 2007 for U.S. Appl. 10/681,018.

Amendment dated Feb. 2, 2004 in Reply to Office Action dated Jul. 29, 2003 for U.S. Appl. No. 09/990,909.

Amendment dated Feb. 7, 2003 in Reply to Office Action dated Jul. 30, 2002 for U.S. Appl. 09/990,909.

Amendment dated Feb. 7, 2009 in Reply to Office Action dated Aug. 18, 2008 for U.S. Appl. No. 10/681,018.
Amendment dated Mar. 1, 2004 in Reply to Office Action dated Aug. 26, 2003 for U.S. Appl. No. 10/041,073.
Amendment dated Mar. 3, 2008 to Restriction Requirement dated Jan. 10, 2008 for U.S. Appl. 11/232,180.
Amendment dated Mar. 4, 2008 in Reply to Office Action dated Nov. 4, 2007 for U.S. Appl. No. 11/213,255.
Amendment dated May 18, 2007 in Reply to Office Action dated Dec. 22, 2006 for U.S. Appl. No. 10/681,018.
Amendment dated May 19, 2008 in Reply to Final Office Action dated Mar. 17, 2008 for U.S. Appl. No. 10/681,018.
Amendment dated Jun. 8, 2007 in Reply to Restriction Requirement dated May 9, 2007 for U.S. Appl. No. 11/213,382.
Amendment dated Jun. 8, 2010 in Reply to Office Action dated Jun. 8, 2010 for U.S. Appl. No. 10/681,018.
Amendment dated Jul. 2, 2008 in Reply to Notice of Non-Compliant Amendment dated Jun. 2, 2008 for U.S. Appl. No. 12/046,252.
Amendment dated Aug. 21, 2008 in Reply to Office Action dated Apr. 21, 2008 for U.S. Appl. No. 11/232,180.
Amendment dated Sep. 24, 2007 in Reply to Restriction Requirement dated Jun. 22, 2007 for U.S. Appl. No. 11/213,255.
Amendment dated Sep. 25, 2008 in Reply to Final Office Action dated Jun. 25, 2008 for U.S. Appl. No. 11/213,255.
Amendment in Response dated May 23, 2003 to Restriction Requirement dated Apr. 23, 2003 for U.S. Appl. 09/990,909.
Brudnak et al. Enzyme-based therapy for autism spectrum disorders—is it worth another look? Med Hypoth. 2002; 58:422-428.
Cruse et al. Illustrated dictionary of immunology. CRC Press, New York. 1995.
Filipek et al. The screening and diagnosis of autistic spectrum disorders. J. of Autism and Dev Disorders. 1999; 29(6).
Final Office Action dated May 11, 2010 for U.S. Appl. No. 11/555,697.
Final Office Action dated Jun. 25, 2008 for U.S. Appl. No. 11/213,255.
Final Office Action dated Jul. 2, 2010 for U.S. Appl. No. 12/046,252.
Final Office Action dated Jul. 27, 2004 for U.S. Appl. No. 09/990,909.
Garcia et al. Detection of giardia lamblia, entamoeba histolytica/ entamoeba dispar, and cryptosporidium parvum antigens in human fecal specimens using the triage parasite panel enzyme immunoassay. Am Soc for Microbiology. 2000; 38(9):3337-3340.
Hendren et al. Mechanistic biomarkers for autism treatment. Medical Hypotheses. 2009; 73:950-954.
International search report and written opinion dated Jan. 18, 2011 for PCT/US2010/057341.
International search report and written opinion dated Feb. 15, 2011 for PCT/US2010/053484.
International search report and written opinion dated Mar. 2, 2010 for PCT/US2010/020253.
International search report and written opinion dated Jun. 9, 2010 for PCT/US2010/030895.
International search report and written opinion dated Sep. 25, 2009 for PCT/US0949374.
International search report and written opnion dated Mar. 5, 2010 for PCT/US2010/020259.
International search report dated Mar. 11, 2002 for PCT/US2001/25343.
International search report dated Jun. 29, 2001 for PCT/US2000/34000.
Lieberman. Pharmaceutical Dosage Forms. vol. 2: Disperse Systems. New York Marcel Dekker, Inc. 1996; 243-258.
Lipase 30, Technical Data sheet, 1 page, Scientific Protein Laboratories LLC Jun. 13, 2005.
Munasinghe et al. Digestive enzyme supplementation for autism spectrum disorders: a double-blind randomized controlled trial. J Autism Dev Disord, Mar. 5, 2010; Epub ahead of print.
Nevo et al. Acute immune polyneuropathies: correlations of serum antibodies to campylobacter jejuni and helicobacter pylori with anti-gm antibodies and clinical patterns of disease. J of Inf diseases. 1997; 175(S2):S154-6.
Notice Non-responsive Amendment dated Sep. 22, 2008 for U.S. Appl. No. 11/232,180.
Notice of Non-Complaint Amendment dated Jun. 2, 2008 for U.S. Appl. No. 12/046,252.
Notice of Non-Compliant Amendment dated May 7, 2007 for U.S. Appl. No. 11/213,255.
Office Action dated Jan. 21, 2011 for U.S. Appl. No. 12/386,051.
Office Action dated Jan. 29, 2002 for U.S. Appl. No. 09/707,395.
Office Action dated Oct. 1, 2001 for U.S. Appl. No. 09/466,559.
Office Action dated Oct. 5, 2010 for U.S. Appl. No. 12/046,402.
Office Action dated Nov. 14, 2007 for U.S. Appl. No. 11/213,255.
Office Action dated Nov. 15, 2010 for U.S. Appl. No. 12/238,415.
Office Action dated Nov. 26, 2001 for U.S. Appl. No. 09/466,559.
Office Action dated Dec. 19, 2005 for U.S. Appl. No. 10/730,567.
Office Action dated Mar. 18, 2008 for U.S. Appl. No. 11/468,379.
Office Action dated Mar. 25, 2008 for U.S. Appl. No. 11/213,382.
Office Action dated Apr. 12, 2010 for U.S. Appl. No. 09/990,909.
Office Action dated Apr. 21, 2008 for U.S. Appl. No. 11/232,180.
Office Action dated Apr. 22, 2003 for U.S. Appl. No. 09/929,592.
Office Action dated May 22, 2002 for U.S. Appl. No. 09/466,559.
Office Action dated Jul. 22, 2010 for U.S. Appl. No. 12/049,613.
Office Action dated Jul. 30, 2002 for U.S. Appl. No. 09/707,395.
Office Action dated Jul. 30, 2002 for U.S. Appl. No. 09/990,909.
Office Action dated Jul. 6, 2010 for U.S. Appl. No. 11/533,818.
Office Action dated Aug. 13, 2002 for U.S. Appl. No. 09/929,592.
Office Action dated Aug. 18, 2008 for U.S. Appl. No. 10/681,018.
Office Action dated Aug. 20, 2010 for U.S. Appl. No. 12/283,090.
Office Action dated Aug. 26, 2003 for U.S. Appl. No. 10/041,073.
Office Action dated Aug. 8, 2007 for U.S. Appl. No. 11/213,382.
Office Action dated Sep. 22, 2004 for U.S. Appl. No. 10/730,567.
Pancreatic Enzyme Concentrate (PEC) Undiluted, Technical Data Sheet. 1 page, Scientific Protein Laboratories LLC Jun. 13, 2005.
Pancreatin 4X USP, Technical Data Sheet, 1 page, Scientific Protein laboratories LLC Jun. 13, 2005.
Perman et al. Role of ph in production of hydrogen from carbohydrates by colonic bacterial flora. J Clin Invest. 1981; 24(4):684-685.
Peters et al. Prevalence of enteric parasites in homosexual patients attending an outpatient clinic. J of Clin Micro. 1986; 24(4):684-685.
Preliminary Amendment dated May 18, 2009 for U.S. Appl. No. 12/046,252.
Response dated Oct. 3, 2006 to Restriction Requirement dated Sep. 12, 2006 for U.S. Appl. No. 10/681,018.
Response dated Apr. 29, 2010 to Notice of Non-Compliant Amendment dated Apr. 27, 2010 for U.S. Appl. No. 12/283,090.
Response dated Jun. 17, 2008 to Advisory Action dated Jun. 3, 2008 for U.S. Appl. No. 10/681,018.
Response dated Jun. 24, 2002 to Restriction Requirement dated May 22, 2002 for U.S. Appl. No. 09/990,909.
Response dated Jun. 7, 2007 to Notice of Non-Compliant Amendment dated May 7, 2007 for U.S. Appl. No. 11/213,255.
Restriction Requirement dated Jan. 10, 2008 for U.S. Appl. No. 11/232,180.
Restriction Requirement dated Oct. 7, 2009 for U.S. Appl. No. 12/283,090.
Restriction Requirement dated Dec. 10, 2009 for U.S. Appl. No. 11/533,818.
Restriction Requirement dated Apr. 23, 2003 for U.S. Appl. No. 09/990,909.
Restriction Requirement dated May 22, 2002 for U.S. Appl. No. 09/990,909.
Restriction Requirement dated May 9, 2007 for U.S. Appl. No. 11/213,382.
Restriction Requirement dated Jun. 22, 2007 for U.S. Appl. No. 11/213,255.
Restriction Requirement dated Sep. 12, 2006 for U.S. Appl. No. 10/681,018.
Sandler et al. Short term benefit from oral vancomycin treatment of regressive-onset autism. J of Child Neuro. 2000; 15(7):42-435.
Schreck et al. Food preferences and factors influecing food selectivity for children with autism spectrum disorders. Res Develop Disabil. 2006; 27:353-363.

Skeels et al. Crytosporidium infection in Oregon public health clinic patients 1985-88: the value of statewide laboratory surveillance. AJPH 1990; 80(3):305-308.

Supplemental Amendment and Response dated Jun. 8, 2010 to Restriction Requirement dated Oct. 7, 2009 for U.S. Appl. No. 12/283,090.

USP (32)-NF(27) 2009, Pancreatin, V.3, pp. 3194-3195.

Wender et al. Prevalence of attention deficit disorder, residual type, and other psychiatric disorders in patients with irritable colon syndrome. Am J Psychiatry. 1983; 140(12):1579-82 Abstract only.

Wohlman et al. Enhancement of drug activity by chymotrypsin, penicillin penetration into granulomatous sesions and inflammatory fluids. Cellular and Molecular Life Sciences. 1969; 25(9):953-954.

Zhang et al. Lactulose-mannitol intestinal permeability test in children with diarrhea caused by rotavirus abd cryptosporidium. J of Pediatric Gastro & Nutrition. 2000; 31(1):16-21.

Stein, et al. Nitrogen Metabolism in normal and hyperkinetic boys. Am J Clin Nutr. 1984; 39:520-524.

Sherwood and Becker, "A new class of high-functionality excipients: Silicified microcrystalline cellulose," *Pharm. Tech.*, Oct. 1998, 22 (10): 78-88.

Seneca and Henderson, "Enhancement Of Brain L-Dopa Concentration With A-Chymotrypsin," Journal of the American Geriatrics Society, 1973, pp. 256-258.

The Alzheimer's Association, "Basics of Alzheimer's Disease" [online], 2005 [retrieved on Sep. 18, 2009], retrieved from: http://www.alz.org/national/documents/brochure_basicsofalz_low/pdf.

Tsang et al., Extragastroduodenal conditions associated with Helicpbacter pylon infection, *Hong Kong Medical Journal*, 1999, 5(2):169-174.

Woodward et al., "Ischaemic enterocolitis complicating idiopathic dysatuonomia," *Gut*, 1998, 43:285-287.

USPTO Office Action in U.S. Appl. No. 10/681,018, mailed Jan. 8, 2010, 21 pages.

Fish & Richardson P.C., Amendment in Reply to Final Office Action dated Apr. 28, 2009 in U.S. Appl. No. 10/681,018 filed Oct. 28, 2009, 20 pages.

USPTO Final Office Action in U.S. Appl. No. 10/681,018, mailed Apr. 28, 2009, 8 pages.

Kristina M. Grasso, Esq. PLLC Amendment in Reply to Action dated Aug. 18, 2008 in U.S. Appl. No. 10/681,018, filed Feb. 7, 2009, 7 pages.

USPTO Office Action in U.S. Appl. No. 10/681,018, mailed Aug. 18, 2008, 6 pages.

Kristina M. Grasso, Esq. PLLC Response to Advisory Action dated Jun. 3, 2008 in U.S. Appl. No. 10/681,018, filed Jun. 17, 2008, 11 pages.

USPTO Advisory Action in U.S. Appl. No. 10/681,018, mailed Jun. 3, 2008, 4 pages.

Kristina M. Grasso, Esq. PLLC Amendment in Reply to Action dated Mar. 17, 2008 in U.S. Appl. No. 10/681,018, filed May 19, 2008, 10 pages.

USPTO Final Office Action in U.S. Appl. No. 10/681,018, mailed Mar. 17, 2008, 10 pages.

Kristina M. Grasso, Esq. PLLC Amendment in Reply to Action dated Aug. 7, 2007 in U.S. Appl. No. 10/681,018, filed Dec. 7, 2007, 11 pages.

USPTO Office Action in U.S. Appl. No. 10/681,018, mailed Aug. 7, 2007, 10 pages.

Maine & Asmus Amendment in Reply to Action dated Dec. 22, 2006 in U.S. Appl. No. 10/681,018, filed May 18, 2007, 11 pages.

USPTO Office Action in U.S. Appl. No. 10/681,018, mailed Dec. 22, 2006, 8 pages.

Maine & Asmus Response to Election/Restriction Requirement dated Sep. 12, 2006 in U.S. Appl. No. 10/681,018, filed Oct. 3, 2006, 6 pages.

USPTO Restriction Requirement in U.S. Appl. No. 10/681,018, mailed Sep. 12, 2006, 5 pages.

USPTO Office Action in U.S. Appl. No. 11/555,697, mailed Aug. 3, 2009, 11 pages.

Kristina M. Grasso, Esq. PLLC Amendment in Reply to Feb. 27, 2009 Final Office i Action in U.S. Appl. No. 11/555,697, filed May 27, 2009, 12 pages.

USPTO Final Office Action in U.S. Appl. No. 11/555,697, mailed Feb. 27, 2009, 13 pages.

Kristina M. Grasso, Esq. PLLC Amendment in Reply to Sep. 25, 2008 Notice of Non-Responsive Amendment in U.S. Appl. No. 11/555,697, filed Oct. 24, 2008, 7 pages.

USPTO Notice of Non-Responsive Amendment in U.S. Appl. No. 11/555,697, mailed Sep. 25, 2008, 2 pages.

Kristina M. Grasso, Esq. PLLC Amendment in Reply to Mar. 28, 2008 Office Action in U.S. Appl. No. 11/555,697, filed Aug. 28, 2008, 10 pages.

USPTO Office Action in U.S. Appl. No. 11/555,697, mailed Mar. 28, 2008, 9 pages.

Kristina M. Grasso, Esq. PLLC Amendment in Reply to Feb. 11, 2008 Notice of Non-Responsive Amendment in U.S. Appl. No. 11/555,697, filed Feb. 29, 2008, 4 pages.

USPTO Notice of Non-Responsive Amendment in U.S. Appl. No. 11/555,697, mailed Feb. 11, 2008, 2 pages.

Kristina M. Grasso, Esq. PLLC Amendment in Reply to Oct. 17, 2007 Restriction Requirement in U.S. Appl. No. 11/555,697, filed Nov. 17, 2007, 6 pages.

USPTO Restriction Requirement in U.S. Appl. No. 11/555,697, mailed Oct. 17, 2007, 9 pages.

USPTO Office Action in U.S. Appl. No. 12/046,252, mailed Sep. 24, 2009, 11 pages.

USPTO Office Action in U.S. Appl. No. 11/232,180, mailed Nov. 25, 2009, 13 pages.

Kristina M. Grasso, Esq. PLLC Amendment in Reply to Notice Non-Compliant Amendment dated Aug. 19, 2009 in U.S. Appl. No. 11/232,180, filed Aug. 19, 2009, 7 pages.

USPTO Notice Non-Compliant Amendment in U.S. Appl. No. 11/232,180, mailed Jun. 19, 2009, 2 pages.

Kristina M. Grasso, Esq. PLLC Amendment in Reply to Mar. 13, 2009 Final Office Action in U.S. Appl. No. 11/232,180, filed Jun. 15, 2009, 12 pages.

USPTO Final Office Action in U.S. Appl. No. 11/232,180, mailed Mar. 13, 2009, 13 pages.

Amendment and Response dated Apr. 7, 2010 in Reply to Restriction Requirement dated Oct. 7, 2009 for U.S. Appl. No. 12/283,090.

Amendment dated Oct. 20, 2008 in Reply to Notice Non-responsive Amendment dated Sep. 22, 2008 for U.S. Appl. No. 11/232,180.

Amendment dated Nov. 13, 2009 in Reply to Final Office Action dated Jul. 27, 2004 for U.S. Appl. No. 09/990,909.

Amendment dated Dec. 12, 2007 in Reply to Office Action dated Aug. 8, 2007 for U.S. Appl. No. 11/213,382.

Amendment dated Dec. 7, 2007 in Reply to Office Action dated Aug. 7, 2007 for U.S. Appo. No. 10/681,018.

Amendment dated Feb. 2, 2004 in Reply to Office Action dated Jul. 29, 2003 for U.S. Appl. No. 09/990,909.

Amendment dated Feb. 7, 2003 in Reply to Office Action dated Jul. 30, 2002 for U.S. Appl. No. 09/990,909.

Amendment dated Feb. 7, 2009 in Reply to Office Action dated Aug. 18, 2008 for U.S. Appl. No. 10/681,018.

Amendment dated Mar. 1, 2004 in Reply to Office Action dated Aug. 26, 2003 for U.S. Appl. No. 10/041,073.

Amendment dated Mar. 24, 2010 in Reply to Final Office Action dated Jul. 2, 2010 for U.S. Appl. No. 12/046,252.

Amendment dated Mar. 3, 2008 to Restriction Requirement dated Jan. 10, 2008 for U.S. Appl. No. 11/232,180.

Amendment dated Mar. 4, 2008 in Reply to Office Action dated Nov. 14, 2007 for U.S. Appl. No. 11/213,255.

Final Office Action dated Nov. 9, 2010 for U.S. Appl. No. 09/990,909.

Garcia et al. Detection of giardia lamblia, entamoeba histolytica/entamoeba dispar, and cryptosporidium parvum antigens in human fecal specimens using the triage parasite panel enzyme immunoassay. Am Soc for Microbiology. 2000; 38(9):3337-3340.

Hendren et al. Mechanistic biomarkers for autism treatment. Medical Hypotheses. 2009; 73:950-954.

International search report and written opinion dated Jan. 18, 2011 for PCT/US2010/057341.

International search report and written opinion dated Feb. 15, 2011 for PCT/US2010/053484.

International search report and written opinion dated Mar. 2, 2010 for PCT/US2010/020253.
International search report and written opinion dated Jun. 9, 2010 for PCT/US2010/030895.
International search report and written opinion dated Sep. 25, 2009 for PCT/US0949374.
International search report and written opnion dated Mar. 5, 2010 for PCT/US2010/020259.
Lieberman. Pharmaceutical Dosage Forms. vol. 2: Disperse Systems. New York Marcel Dekker, Inc. 1996; 243-258.
Lipase 30, Technical Data sheet, 1 page, Scientific Protein Laboratories Llc Jun. 13, 2005.
Munasinghe et al. Digestive enzyme supplementation for autism spectrum disorders: a double-blind randomized controlled trial. J Autism Dev Disord. Mar 5 1010; Epub ahead of print.
Nevo et al. Acute immune polyneuropathies: correlations of serum antibodies to campylobacter jejuni and helicobacter pylori with anti-gm antibodies and clinical patterns of disease. J of Inf diseases. 1997; 175(S2):S154-6.
Notice Non-responsive Amendment dated Sep. 22, 2008 for U.S. Appl. No. 11/232,180.
Notice of Non-Complaint Amendment dated Jun. 2, 2008 for U.S. Appl. No.12/046,252.
Notice of Non-Compliant Amendment dated Apr. 27, 2010 for U.S. Appl. No. 12/283,090.
Notice of Non-Compliant Amendment dated May 7, 2007 for U.S. Appl. No. 11/213,255.
Office Action dated Jun. 30, 2004 for U.S. Appl. No. 10/730,567.
Office Action dated Jul. 29, 2003 for U.S. Appl. No. 09/990,909.
Office Action dated Aug. 18, 2008 for U.S. Appl. No. 09/929,592.
Office Action dated Aug. 20, 2010 for U.S. Appl. No. 10/681,018.
Pancreatic Enzyme Concentrate (PEC) Undiluted, Technical Data Sheet. 1 page, Scientific Protein Laboratories LLC Jun. 13, 2005.
Pancreatin 4X USP, Technical Data Sheet, 1 page, Scientific Protein laboratories LLC Jun. 13, 2005.
Perman et al. Role of ph in production of hydrogen from carbohydrates by colonic bacterial flora. J Clin Invest. 1981; 24(4):684-685.
Levy, et al. Relationship of dietary intake to gastrointestinal symptoms in children with autistic spectrum disorders. Biol Psychiatry. Feb 15, 2007;61(4):492-7.
Notice of Allowance dated Apr. 29, 2011 for U.S. Appl. No. 12/046,402.
Office Action dated Apr. 27, 2011 for U.S. Appl. No. 10/681,018.
Office Action dated Apr. 28, 2011 for U.S. Appl. No. 12/283,090.
Sturmey. Secretin is an ineffective treatment for pervasive developmental disabilities: a review of 15 double-blind randomized controlled trials. Res Dev Disabil. Jan-Feb 2005 ;26(1):87-97.
Amendment dated Mar. 24, 2010 in Reply to Final Office Action dated Sep. 24, 2009 for U.S. Appl. No. 12/046,252.
Ang, et al. Biological role and regulation of the universally conserved heat shock proteins. J Biol Chem. Dec 25, 1991;266(36):24233-6.
Arribas, et al. A comparative study of the chymotrypsin-like activity of the rat liver multicatalytic proteinase and the ClpP from *Escherichia coli*. J Biol Chem. Oct 5, 1993;268(28):21165-71. abstract only.
Arrigo, et al. Expression of heat shock proteins during development in Drosophila. Results Probl Cell Differ. 1991;17:106-19. abstract only.
Austic. Development and adaptation of protein digestion. J Nutr. May 1985;115(5):686-97.
Awazuhara, et al. Antigenicity of the proteins in soy lecithin and soy oil in soybean allergy. Clin Exp Allergy. Dec. 1998;28(12):1559-64.
Beilmann, et al. Neoexpression of the c-met/hepatocyte growth factor-scatter factor receptor gene in activated monocytes. Blood. Dec. 1, 1997;90(11):4450-8.
Borowitz, et al. Use of pancreatic enzyme supplements for patients with cystic fibrosis in the context of fibrosing colonopathy. Consensus Committee. J Pediatr. Nov. 1995; 127(5):681-4.
Boyd, et al. Positively charged amino acid residues can act as topogenic determinants in membrane proteins. Proc Natl Acad Sci U S A. Dec. 1989;86(23):9446-50.

Bruhat, et al. Amino acid limitation induces expression of CHOP, a CCAAT/enhancer binding protein-related gene, at both transcriptional and post-transcriptional levels. J Biol Chem. Jul. 11, 1997;272(28):17588-93.
Carroccio, et al. Secondary impairment of pancreatic function as a cause of severe malabsorption in intestinal giardiasis: a case report. Am J Trop Med Hyg. Jun. 1997; 56(6): 599-602.
Carroccio, et al. Secretin-cerulein test and fecal chymotrypsin concentration in children with intestinal giardiasis. Int J Pancreatol. Oct. 1993;14(2):175-80.
Cassidy, et al. A new concept for the mechanism of action of chymotrypsin: the role of the low-barrier hydrogen bond. Biochemistry. Apr. 15, 1997;36(15):4576-84.
Chen, et al. Identification of two lysosomal membrane glycoproteins. J Cell Biol. Jul. 1985;101(1):85-95.
Corring, et al. Development of digestive enzymes in the piglet from birth to 8 weeks. I. Pancreas and pancreatic enzymes. Nutr Metab. 1978;22(4):231-43.
Couet, et al. Identification of peptide and protein ligands for the caveolin-scaffolding doinain. Implications for the interaction of caveolin with caveolae-associated proteins. J Biol Chem. Mar. 7, 1997;272(10):6525-33.
Craig, et al. Heat shock proteins: molecular chaperones of protein biogenesis. Microbiol Rev. Jun. 1993;57(2):402-14.
Croonenberghs, et al. Peripheral markers of serotonergic and noradrenergic function in post-pubertal, caucasian males with autistic disorder. Neuropsychopharmacology. Mar. 2000;22(3):275-83.
Edelson, et al. 3-Cyclohexene-l-glycine, an Isoleupine Antagonist. J. Am. Chem. Soc. 1958; 80(11):2698-2700.
Ethridge, et al. Acute pancreatitis results in induction of heat shock proteins 70 and 27 and heat shock factor-1. Pancreas. Oct. 2000;21(3):248-56. abstract only.
Fafournoux, et al. Amino acid regulation of gene expression. Biochem J. Oct. 1, 2000;351(Pt 1):1-12.
Fallingborg, et al. Measurement of gastrointestinal pH and regional transit times in normal children. J Pediatr Gastroenterol Nutr. Aug. 1990;11(2):211-4.
Fitzsimmons, et al. High-dose pancreatic-enzyme supplements and fibrosing colonopathy in children with cystic fibrosis. N. Engl J Med. May 1, 1997;336(18):12839.
Gardner. Absorption of intact peptides: studies on transport of protein digests and dipeptides across rat small intestine in vitro. Q J Exp Physiol. Oct. 1982;67(4):629-37.
Garner Jr, et al. Porcine Pancreatic Lipase—A Glycoprotein. J Biol Chem. Jan. 25, 1972;247(2):561-5.
Giglio, et al. Failure to thrive: the earliest feature of cystic fibrosis in infants diagnosed by neonatal screening. Acta Paediatr. Nov. 1997;86(11):1162-5.
Goff, et al. Production of abnormal proteins in *E. coli* stimulates transcription of lon and other heat shock genes. Cell. Jun. 1985;41(2):587-95. abstract only.
Green, et al. Amino-terminal polymorphisms of the human beta 2-adrenergic receptor impart distinct agonist-promoted regulatory properties. Biochemistry. Aug. 16, 1994 ;33(32):9414-9.
Gupta, et al. Th1- and Th2-like cytokines in CD4+ and CD8+ T cells in autism. J Neuroimmunol. May 1, 1998;85(1):106-9.
Hadjivassiliou, et al. Does cryptic gluten sensitivity play a part in neurological illness? Lancet. Feb. 10, 1996;347(8998):369-71.
Horvath, et al. Gastrointestinal abnormalities in children with autistic disorder. J Pediatr. Nov. 1999;135(5):559-63.
Huang, et al. Apoptotic cell death in mouse models of GM2 gangliosidosis and observations on human Tay-Sachs and Sandhoff diseases. Hum Mol Genet. Oct. 1997;6(11):1879-85.
Huang, et al. Mapping of the human APOB gene to chromosome 2p and demonstration of a two-allele restriction fragment length polymorphism. Proc Natl. Acad Sci U S A. Feb, 1986;83(3):644-8.
Juhl. Fibromyalgia and the serotonin pathway. Ahern Med Rev. 1998; 3(5):367-375.
Koller, et al. Falls and Parkinson's Disease (Abstract). Clin Neuropharmacol. 1989; 12(2):98-105. abstract only.
Lloyd. Lysosome membrane permeability: implications for drug delivery. Adv Drug Deliv Rev. Mar. 30, 2000;41(2):189-200. abstract only.

Luedtke, et al. Cathepsin A is expressed in a cell- and region-specific manner in the testis and epididymis and is not regulated by testicular or pituitary factors. J Histochem Cytochem. Aug. 2000;48(8):1131-46.

Mannino, et al. Surveillance for asthma—United States, 1960-1995. MMWR CDC Surveill Summ, Apr. 24, 1998;47(1):1-27.

McCormack, et al. Localization of the disulfide bond involved in post-translational processing of glycosylasparaginase and disrupted by a mutation in the Finnish-type aspartylglycosaminuria J Biol Chem. Feb. 17, 1995;270(7):3212-5.

Melmed, et al. Metabolic markers and gastrointestinal symptoms in children with autism and related disorders. J Pediatr Gast Nutr. 2000; 31:S31-S32.

Mononen, et al. Aspartylglycosaminuria in the Finnish population: identification of two point mutations in the heavy chain of glycoasparaginase. Proc Natl Acad Sci U S A. Apr. 1, 1991;88(7):2941-5.

Neuer, et al. The role of heat shock proteins in reproduction. Hum Reprod Update. Mar.-Apr. 2000;6(2):149-59.

Notice of Allowance dated May 23, 2011 for U.S Appl. No. 09/990,909.

Notice of Non-Compliant Amendment dated Apr. 27, 2010 for U.S. Appl. No. 12/283,090.

Office Action dated May 24, 2011 for U.S. Appl. No. 12/487,864.

Puri, et al. Isolated segmental duodenal ganglionosis. Indian Journal of Radiology and Imaging. 2000; 153-154.

Rider, et al. Perspective of biochemical research in the neuronal ceroid-lipofuscinosis. Am J Med Genet. Feb. 15, 1992;42(4):519-24. abstract only.

Rottier, et al. Lack of PPCA expression only partially coincides with lysosomal storage in galactosialidosis mice: indirect evidence for spatial requirement of the catalytic rather than the protective function of PPCA. Hum Mol Genet. Oct. 1998;7(11):1787-94.

Sabra, et al. Linkage of ileal-lymphoid-nodular hyperplasia (ILNH), food allergy and CNS developmental: evidence for a non-IgE association. Ann Aller Asth Immunol. 1999; 82:8. not submitted.

Sandler, et al. Lack of benefit of a single dose of synthetic human secretin in the treatment of autism and pervasive developmental disorder. N Engl J Med. Dec. 9, 1999;341(24):1801-6.

Schafer, et al. Stress kinases and heat shock proteins in the pancreas: possible roles in normal function and disease. J Gastroenterol. 2000;35(1):1-9. abstract only.

Singh, et al. Plasma increase of interleukin-12 and interferon-gamma. Pathological significance in autism, J Neuroimmunol. May 1996;66(1-2):143-5.

Stein, et al. Nitrogen metabolism in normal and hyperkinetic boys. Am J Clin Nutr. Apr. 1984;39(4):520-4.

Steinherz, et al. Patterns of amino acid efflux from isolated normal and cystinotic human leucocyte lysosomes. J Biol Chem. Jun. 10, 1982;257(11):6041-9.

Stoll, et al. Enteral nutrient intake level determines intestinal protein synthesis and accretion rates in neonatal pigs. Am J Physiol Gastrointest Liver Physiol. Aug. 2000;279(2):G288-94.

Strader, et al. Publication Structural basis of β-adrenergic receptor function. FASEB J. May 1989;3(7):1825-32.

Thomas, et al. Defective protein folding as a basis of human disease. Trends Biochem Sci. Nov. 1995;20(11):456-9.

Vilanova, et al. Preparative isolation of the two forms of pig pancreatic pro-(carboxypeptidase A) and their monomeric carboxypeptidases A. Biochem J. Aug. 1, 1985;229(3):605-9.

Volkmar, et al. Practice parameters for the assessment and treatment of children, adolescents, and adults with autism and other pervasive developmental disorders. American Academy of Child and Adolescent Psychiatry Working Group on Quality Issues. J Am Acad Child Adolesc Psychiatry. (PART 1) Dec. 1999;38(12 Suppl):32S-54S.

Volkmar, et al. Practice Parameters for the Assessment and Treatment of Children, Adolescents, and Adults with Autism and other Pervasive Developmental Disorders. American Academy of Child and Adolescent Psychiatry. J Am Acad Child Adolesc Psychiatry. (PART 2) Dec. 1999;38(12):1611-6.

Wakefield, et al. Enterocolitis in children with developmental disorders. Am J Gastroenterol. Sep. 2000;95(9):2285-95.

Wakefield, et al. Ileal-lymphoid-nodular hyperplasia, non-specific colitis, and pervasive developmental disorder in children. Lancet. Feb. 28, 1998;351(9103):637-41.

Walsh, et al. Heat shock and the role of the HSPs during neural plate induction in early mammalian CNS and brain development. Cell Mol Life Sci. Feb. 1997;53(2):198-211.

Weintraub, et al. Morphometric studies of pancreatic acinar granule formation in NCTR-Balb/c mice. J Cell Sci. May 1992;102 ( Pt 1):141-7.

Williams, et al. Eating habits of children with autism. Pediatr Nurs. May-Jun. 2000;26(3):259-64.

Youngberg, et al. Comparison of gastrointestinal pH in cystic fibrosis and healthy subjects. Dig Dis Sci. May 1987;32(5):472-80.

Yuan, et al. Freeze-Thaw Stability of Three Waxy Maize Starch Pastes Measured by Centrifugation and Calorimetry. Cereal Chem. 1998; 75(4):571-573.

Zeiner, et al. Mammalian protein RAP46: an interaction partner and modulator of 70 kDa heat shock proteins. EMBO J. Sep 15, 1997;16(18):5483-90.

Notice of Allowance dated Jun. 27, 2011 for U.S Appl. No. 12/238,415.

Notice of Allowance dated Jun. 30, 2011 for U.S. Appl. No. 09/990,909.

Notice of Allowance dated Jul. 8, 2011 for U.S. Appl. No. 12/046,402.

Cichoke, et al. The complete book of enzyme therapy. Penguin. 1998: 39, 42, 47, 50, and 53.

Office action dated Jun. 29, 2011 for U.S. Appl. No. 11/555,697.

Figure 3
DE and Parkinson's - Tremors

Figure 6
Fecal Chymotrypsin Levels in Parkinson's v. non-Parkinson's subjects

METHODS OF TREATING AND DIAGNOSING PARKINSONS DISEASE AND RELATED DYSAUTONOMIC DISORDERS

CROSS-REFERENCE TO RELATED APPLICATIONS

This application is a continuation application of U.S. application Ser. No. 12/046,252, filed on Mar. 11, 2008, which is a divisional application of U.S. application Ser. No. 11/555,697, filed Nov. 2, 2006, which is a continuation-in-part of U.S. application Ser. No. 10/730,567, filed Dec. 8, 2003, now U.S. Pat. No. 7,138,123, which is a continuation of U.S. application Ser. No. 09/929,592, filed Aug. 14, 2001, now U.S. Pat. No. 6,660,831, which claims the benefit of U.S. Provisional Application No. 60/224,991, filed Aug. 14, 2000. Each of these applications are herein incorporated in their entirety by reference.

FIELD OF THE INVENTION

The present invention generally relates to a method for treating Parkinson's disease and related dysautonomic disorders and a method for diagnosing individuals with Parkinson's disease or related dysautonomic disorders. More particularly, the invention relates to a diagnosis method of analyzing a stool sample of an individual for the presence of a biological marker (or marker compound) that provides an indication of whether the individual has, or can develop, Parkinson's disease or a related dysautonomic disorder, as well as a therapeutic method for treating Parkinson's disease or a related dysautonomic disorder by the administration of pancreatic/digestive enzymes.

BACKGROUND OF THE INVENTION

The nervous system of the body is comprised of two separate systems, the central nervous system and the peripheral nervous system. The peripheral nervous system is comprised of the somatic or "voluntary" nervous system and the autonomic or "automatic" nervous system.

The autonomic nervous system is further broken down into the parasympathetic, sympathetic, and enteric nervous systems. Additionally, it is known that the adrenal glands help to support the sympathetic responses of the autonomic nervous system and the enteric nervous system deals exclusively with the gastrointestinal system. With some overlap they each control various autonomic functions of the body through regulation so neurotransmitter releases which affect nervous control Acetylcholine is a neurotransmitter used by the parasympathetic nervous system, while nor epinephrine is utilized by the sympathetic nervous system. The adrenal glands secrete epinephrine which help to support the sympathetic nervous system. Norepinephrine and epinephrine together with a substance most affected in Parkinson's disease; dopamine, make up a category of hormones known as the catecholamines.

The enteric nervous system exerts tremendous control over the digestive processes of the body, including gastrointestinal blood flow, secretion absorption, and overall breakdown of food. The enteric nervous system contains a significant number of neurons, thought to be as numerous as those found in the central nervous system. The enteric nervous system is comprised of three types of neurons: sensory, motor, and interneurons. While the sensory neurons are able to determine the environment of the lumen including chemical, ph, thermal and mechanical changes within the lumen, the motor neurons, including those to the pancreatic exocrine cells, control digestion and play a major role in the breakdown of food and the ultimate absorption of nutrients.

There are two network of nerve plexuses which constitute the enteric nervous system: the myenteric plexus and the submucous plexus. The two plexuses extend from the esophagus to the anus and thus run almost the entire route of the gastrointestinal system.

The submucous plexus, which is not continuous throughout the gastrointestinal tract, is located in the submucosal layer of the gastrointestinal tract. Its primary function is to assess the luminal activity of the GI system, and therefore exert tremendous control over GI blood flow, secretions into the lumen and absorption rates of such things as nutrients, water, and hormones such as secretin which is secreted into the blood stream as a result of the enteric nervous systems determination of low Ph of the bolus of food entering the small intestine. This further ultimately determines the role of the pancreatic/digestive enzymes.

The myenteric plexus controls digestive motility and is located in between the longitudinal and circular layers of muscle in the tunica muscularis. It is this segment of the enteric nervous system which may be initially affected in Parkinson's disease.

The overall digestive process includes the communication between the autonomic (enteric) nervous system and the central nervous system as digestion does not happen solely as a function of the autonomic nervous system. Additionally, there are significant enteric hormones that affect digestion, including secretin, which are under the control of the autonomic nervous system. From the autonomic nervous system, there is an overall increase in the stimulation of digestion from the parasympathetic branch of the autonomic nervous system which occurs mainly through the secretion of the neurotransmitter acetylcholine, while norepinephrine, secreted by the sympathetic nervous system decreases digestion in the gastrointestinal tract.

Dysautonomias are diseases and syndromes that relate to the autonomic nervous system of the individual. Hence in individuals afflicted with dysautonomias, many normal and automatic functions of the body are left with poor function or little to no function at all.

There are a plethora of dysautonomic disorders in which the symptoms of autonomic dysfunction are manifest. For instance, Parkinson's disease is marked by mild to severe autonomic dysfunction including changes in gait, tremor, discoordination, increased salivary flow, and overall loss of autonomic function. Additionally, changes in executive function are typically noted in a Parkinson's patient, often allowing the patient to appear as having Alzheimer's disease and resulting in misdiagnosis. Executive function disorders are also found in autistic children.

It has been noted that a lack of secretin response, which is directly under the control of the enteric nervous system, may underlie may other conditions. Further, the use of secretin directly as a therapeutic agent may be efficacious as in the case of those with familial dysautonomia.

Parkinson's disease is widespread throughout the Western hemisphere and was first reported by physician James Parkinson in 1817. Parkinson's disease is first detected as a tremor in a limb, and ultimately progresses to include 3 manifestations: (i) rigidity, which is characterized by "cog-wheel" like movement and "lead-pipe" rigidity; (ii) bradykinesia or slowness in movement, and (iii) postural instability associated with a stooped stance and an impaired gait. These altered movements are features of the motor dysfunction, but in addition there can also be a mental impairment in as many as 40% of all Parkinson's patients.

It is known that Parkinson's disease is caused by a deficient state of levo-dopamine in the brain. More specifically, levo-dopa induced dyskinesis in Parkinson's patients is thought to be a result of denervation of the substantia nigra. To date, medical science has not found a substrate that would allow an injectable form of levo-dopa to reach the brain and successfully cross the blood brain barrier. The current dopamine replacement therapy is aimed at either direct replacement or mimicking the action at the dopamine receptor sites in the brain. Sinemet™. and Sinemet CR™ are the two major drugs suited to that end. While the levo-dopa therapy can create some beneficial changes initially, those changes generally wane over time, and produce other problems such as severe sleep disturbance, dyskinesias, and constant nausea. Medical approaches to Parkinson's disease include surgical destruction of the tissue of the brain and the insertion of microelectrodes (deep brain electrical stimulation) to effected portions of the brain. The insertion of electrodes has the advantage of being reversible. These interventions, however, are generally transient and neither produces a permanent change in the Parkinsonian state nor reverses the effects of the disease.

Some authors suggest that Parkinson's disease is a multifactor, neurodegenerative disorder, which evolves due to excessive oxidation. The substantia nigra is susceptible to oxidative damage which supports this theory of the formation of Parkinson's disease. Abnormalities of the oxidative phosphorylation impair the mitochondria of the substantia nigra, and intensify free radical generation.

While the dyskinesias and loss of executive functioning of the brain receive the most significant mention with respect to Parkinson's disease, other physical manifestations exist that are associated with autonomic dysfunction which are often poorly understood. Some of these manifestations include, e.g.: esophageal reflux, diarrhea, and other gastrointestinal dysfunction. In addition, excessive sweating, sleep disturbances and other symptoms of Parkinson's disease are very similar to those found in familial dysautonomia.

It has long been held that protein restricted diets, timed protein intake diets, or low protein diets were essential for the absorption of certain medications, especially levo-dopa, in the patient afflicted with Parkinson's disease. Many studies have demonstrated the possibility that the large neutral amino acids (tryptophan, valine, isoleucine, leucine, tyrosine, phenylalanine) may interfere with the absorption of the l-dopamine. Numerous studies have been performed and much postulation has been made about various diets. It has long been held by the inventor that there was a decrease in protein digestion in the dysautonomic patient, including those with Parkinson's disease. This lack of protein digestion would therefore necessitate an alteration in the protein intake in individuals with this type of dysfunction, including a decrease in the ingestion of certain proteins which may be difficult to digest without the presence of the necessary digestive enzyme and/or proper functioning of the secretin mechanism, and the over-ingestion of protein to make up for that which is not digested when there in an apparent impairment in protein digestive function. For example, if an individual needed 40 grams of protein a day to sustain function, but had only a mechanism which was 10% effective then the individual would gravitate toward a diet which was higher in protein and protein which would be easier to digest.

This fact has recently been demonstrated in a paper found in *Movement Disorders: Protein Intake in Parkinsonian patients using the EPIC food frequency questionnaire* by Marczewska on Apr. 18, 2006. In this paper, 45 Parkinson's patients were evaluated using the EPIC food questionnaire. While average caloric intake was normal in the Parkinson's patients, they consumed significantly higher amounts of protein (mainly in the form of vegetable proteins). The overall protein intake was 50% higher than the recommended daily allowance (1.2 g/kg vs. 0.8 g/kg). More importantly, it showed that the more severe the symptoms of the patient, the greater the protein intake by the patient.

Further, chymotrypsin appears to continue to be a biomarker for those with Parkinson's disease as the chymotrypsin cleaves only essential amino acids. If there is a dearth of chymotrypsin, then the essential amino acids needed by the body will not be available, and a greater ingestion of protein may be needed in order to attain sufficient essential amino acids.

Accordingly, in view of such findings, a method for determining whether an individual suffering from a dysautonomic disorder and/or any disorder comprising dysautonomic components will benefit from the administration of secretin, or pancreatic/digestive enzymes, would be highly advantageous. In addition, a method for aiding in the diagnosis of individuals who may develop Parkinson's disease and related conditions or symptoms is highly desirable.

SUMMARY OF THE INVENTION

The present invention is directed to methods for aiding in the diagnosis of Parkinson's disease and related disorders including, but not limited to Familial Dysautonomia (FD) (or Riley-Day Syndrome), orthostatic intolerance syndrome including mitral value prolapse, postural tachycardia syndrome 35 (POTS), and idiopathic hypovolemia, and Diabetic autonomic failure, and for treating individuals diagnosed as having Parkinson's disease or related disorders including, but not limited to Familial Dysautonomia (FD) (or Riley-Day Syndrome)orthostatic intolerance syndrome including mitral value prolapse, postural tachycardia syndrome 35 (POTS), and idiopathic hypovolemia, and Diabetic autonomic failure.

In one embodiment, a method is provided for treating Parkinson's disease patients, including those who are likely to develop the disorder or those who presently have the disorder, through the administration of digestive/pancreatic enzymes.

In another embodiment, a diagnostic method is provided for determining whether an individual has, or may develop, Parkinson's disease or related disorders and for determining whether an individual will benefit from the administration of pancreatic/digestive enzymes to treat the dysautonomic disorder. In one embodiment, the diagnostic method analyzes a compound in a stool sample of an individual and correlates the analysis of the compound with a dysautonomic disorder or condition or the lack thereof. In one embodiment, the compound to be analyzed is a pancreatic enzyme, such as chymotrypsin, or any compound that provides an indication of either protein digestion or metabolism, pancreatic function, or an inflammatory process, or a combination thereof. In one embodiment, the analysis determines a quantitative level of the compound in the stool.

In a further embodiment, a method for treating a Parkinson's patient with digestive/pancreatic enzymes involves administering an effective amount of digestive/pancreatic enzymes to an individual having the disorder in order to improve a symptom of the disorder.

In yet another embodiment, a method for treating a Parkinson's patient with digestive enzymes/pancreatic enzymes involves analyzing a compound in a stool sample of the individual in which the administration of the digestive enzymes/pancreatic enzymes is based on the analysis of the stool sample. In one embodiment, the compound to be analyzed comprises a pancreatic enzyme, such as chymotrypsin, or any compound that provides an indication of either protein digestion or metabolism, pancreatic function, or an inflammatory process, or a combination thereof.

In yet a further embodiment, a process for analyzing the stool sample involves measuring a quantitative level of a pancreatic enzyme, such as chymotrypsin, present in the stool sample and comparing the measured quantitative level with at least one threshold level to determine the efficacy of the digestive enzyme/pancreatic enzyme administration to the individual. In one embodiment, the threshold level is based on a level of the pancreatic enzyme associated with at least one other individual of the same approximate age that does not have Parkinson's disease.

In an additional embodiment, a formulation of digestive enzymes/pancreatic enzymes is provided which is efficacious for the treatment of Parkinson's disease and related disorders.

The features and advantages described herein are not all-inclusive and, in particular, many additional features and advantages will be apparent to one of ordinary skill in the art in view of the drawings, specification, and claims. Moreover, it should be noted that the language used in the specification has been principally selected for readability and instructional purposes, and not to limit the scope of the inventive subject matter.

DETAILED DESCRIPTION

The present invention is directed to methods for aiding in the diagnosis of dysautonomic disorders and dysautonomic conditions, and for treating individuals diagnosed as having a dysautonomic disorder and other disorders having dysautonomic components. In one embodiment, a method is provided for determining the presence of abnormal protein digestion and/or pancreatic dysfunction of an individual, especially a child, by analyzing a stool sample of the individual for the quantitative levels of one or more pancreatic enzymes including, but not limited to, chymotrypsin, so as to determine if the individual has, or may develop, a dysautonomic disorder or condition. In another embodiment, a method is provided for determining whether the individual is likely to benefit from the administration of secretin, CCK, VIP, digestive enzymes, other peptides, and/or neuropeptides. Until now, there has been no clear biological marker for dysautonomic disorders or conditions to allow early diagnosis or screening of such disorders or conditions.

It has been discovered by the inventor herein that a population of individuals suffering from dysautonomic disorders such as Parkinson's disease have abnormal or pathologic levels of pancreatic enzymes such as chymotrypsin in their stools. It is postulated that in dysautonomic syndromes, the partial paresis of the gastrointestinal tract, and therefore the lack of functioning of the secretory cells of the proximal small intestine, preclude the proper formation and/or release of secretin. It is further postulated that this abnormal protein digestion, as reflected by the low levels of pancreatic enzymes such as chymotrypsin, can be improved by the administration of secretin, CCK, VIP, other neuropeptides, peptides, and/or digestive enzymes to thereby ameliorate the symptoms of dysautonomic conditions. Indeed, as a low measure of fecal chymotrypsin, for example, expresses an abnormality of protein digestion and/or pancreatic dysfunction, it is postulated that an improvement of protein digestion to promote normal growth and development of an individual suffering from a dysautonomic disorder or dysautonomic condition by the administration of secretin, CCK, VIP, other neuropeptides and/or peptides and/or digestive enzymes, can ameliorate the dysautonomic symptoms.

In one embodiment, a stable preparation of digestive/pancreatic enzymes is formed into a dosage formulation containing a therapeutically effective amount of a protease, an amylase, and/or a lipase. The formulation may include additional enzymes, such as pancreatin, chymotrypsin, trypsin, papain and/or papaya. The dosage formulation may be administered by an oral preparation including, but not limited to, an encapsulated tablet, mini-tabs, microcapsule, mini-capsule, time released capsule, sprinkle or other methodology. In one embodiment, the oral preparation is encapsulated using PROSOLV® technology. Alternatively, the oral preparation may be encapsulated using enteric coating, lipid encapsulation, direct compression, dry granulation, wet granulation, and/or a combination of these methods.

The dosage formulations may be as follows (USP=U.S. Pharmacopeia):

Example 1

| | | |
|---|---|---|
| Amylase | 10,000-70,000 | USP units/dose |
| Protease | 10,000-80,000 | USP units/dose |
| Lipase | 4,000-40,000 | USP units/dose |
| Pancreatin | 2,000-6,000 | USP units/dose |
| Chymotrypsin | 2-5 | mg |
| Trypsin | 60-100 | mg |
| Papain | 3,000-30,000 | USP units/dose |
| Papaya | 30-500 | mg |

Example 2

| | | |
|---|---|---|
| Protease | 40,000 | USP units/dose |
| Chymotrypsin | 2-7 | mg |
| Trypsin | 60-100 | mg |
| Papaya | 30-500 | mg |

Example 3

| | | |
|---|---|---|
| Amylase | 30,000 | USP units/dose |
| Protease | 40,000 | USP units/dose |
| Lipase | 30,000 | USP units/dose |
| Chymotrypsin | 2-7 | mg |
| Papaya | 30-500 | mg |

Example 4

| | | |
|---|---|---|
| Amylase | 30,000 | USP units/dose |
| Protease | 40,000-80,000 | USP units/dose |
| Lipase | 30,000-80,000 | USP units/dose |
| Chymotrypsin | 2 | mg |
| Papain | 6,000-30,000 | USP units/dose |

Other combinations of digestive enzymes may also be used. These enzymes can be in the form of animal or plant derivatives, natural or synthetic.

In a study conducted by the inventor, sixteen subjects diagnosed with Parkinson's disease and ranging in age from 41 to 71 were examined were examined. Physical symptoms of the disease, such as constipation, lack of bowel movements, tremors, falling, and an inability to walk were monitored and measured over a period of 180 days. The subjects were given a dosage of digestive enzymes 3-5 per day. The dosages were administered in the form of encapsulated tablets, capsules, and sprinkles. The dosages were taken with meals and snacks. The digestive enzyme dosage included, but was not limited to, one or more of the following: amylases, proteases, pancreatin, papain, papaya, lipases, chymotrypsin, and trypsin.

Ninety-five percent of adults have bowel movements between three and 21 times per week, and this would be considered normal. The most common pattern is one bowel movement a day. However, some people do not have bowel movements every day or the same number of bowel movements each day. Medically speaking, constipation usually is defined as fewer than three bowel movements per week. Severe constipation is defined as less than one bowel movement per week.

Figure 1:
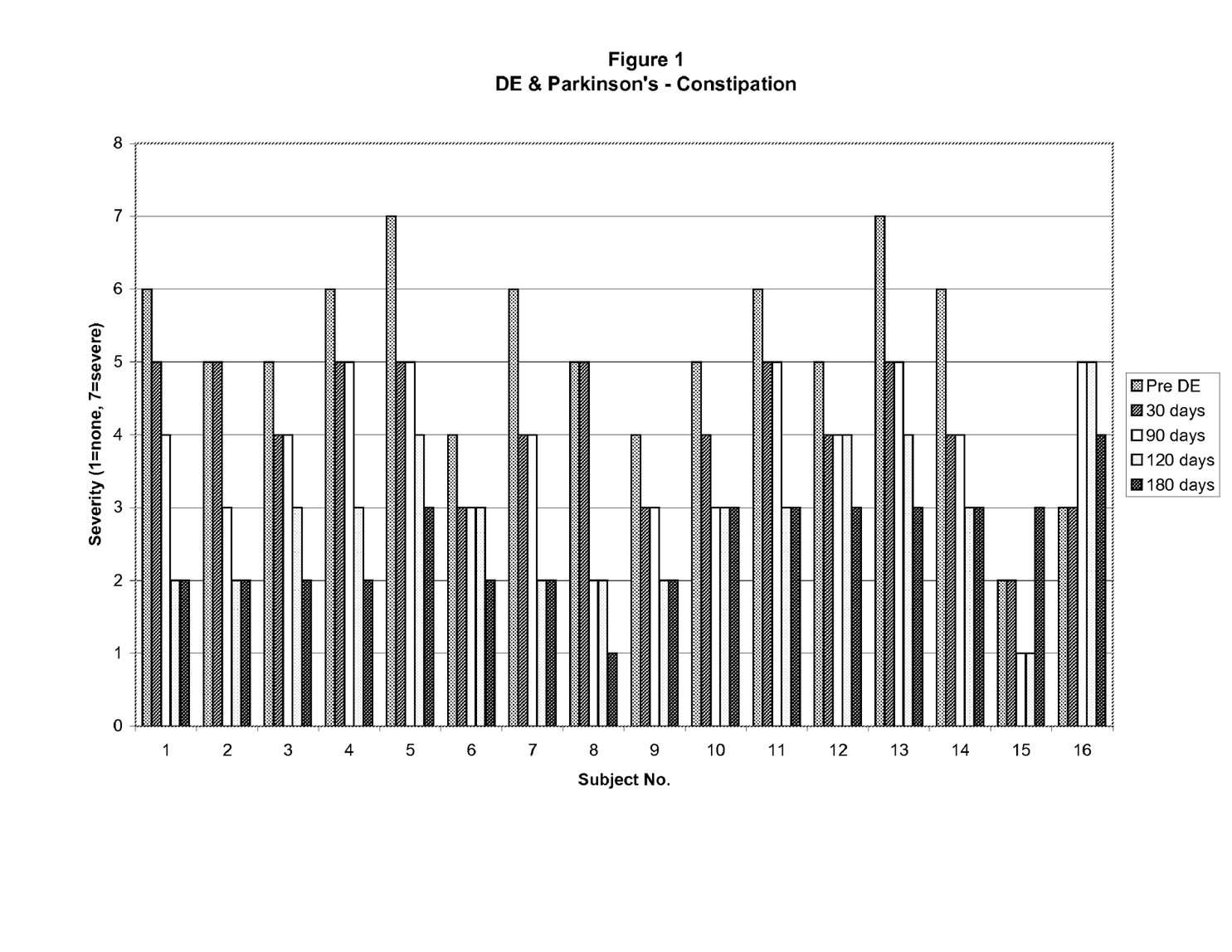
FIG. 1 is a graph demonstrating the decrease in occurrences of constipation in Parkinson's patients after administration of digestive enzymes over a period of 180 days.

Referring to FIG. 1, a majority of the subjects experienced moderate to severe constipation prior to any treatment with digestive enzymes. The severity of the constipation was measured on a scale of 1 to 7, with 1 equaling no constipation and 7 equaling severe constipation. The subjects were monitored at 30, 90, 120 and 180 day intervals. Over the course of the 180 day treatment, the severity of the constipation decreased from severe to moderate to mild in the majority of the subjects.

Figure 2:
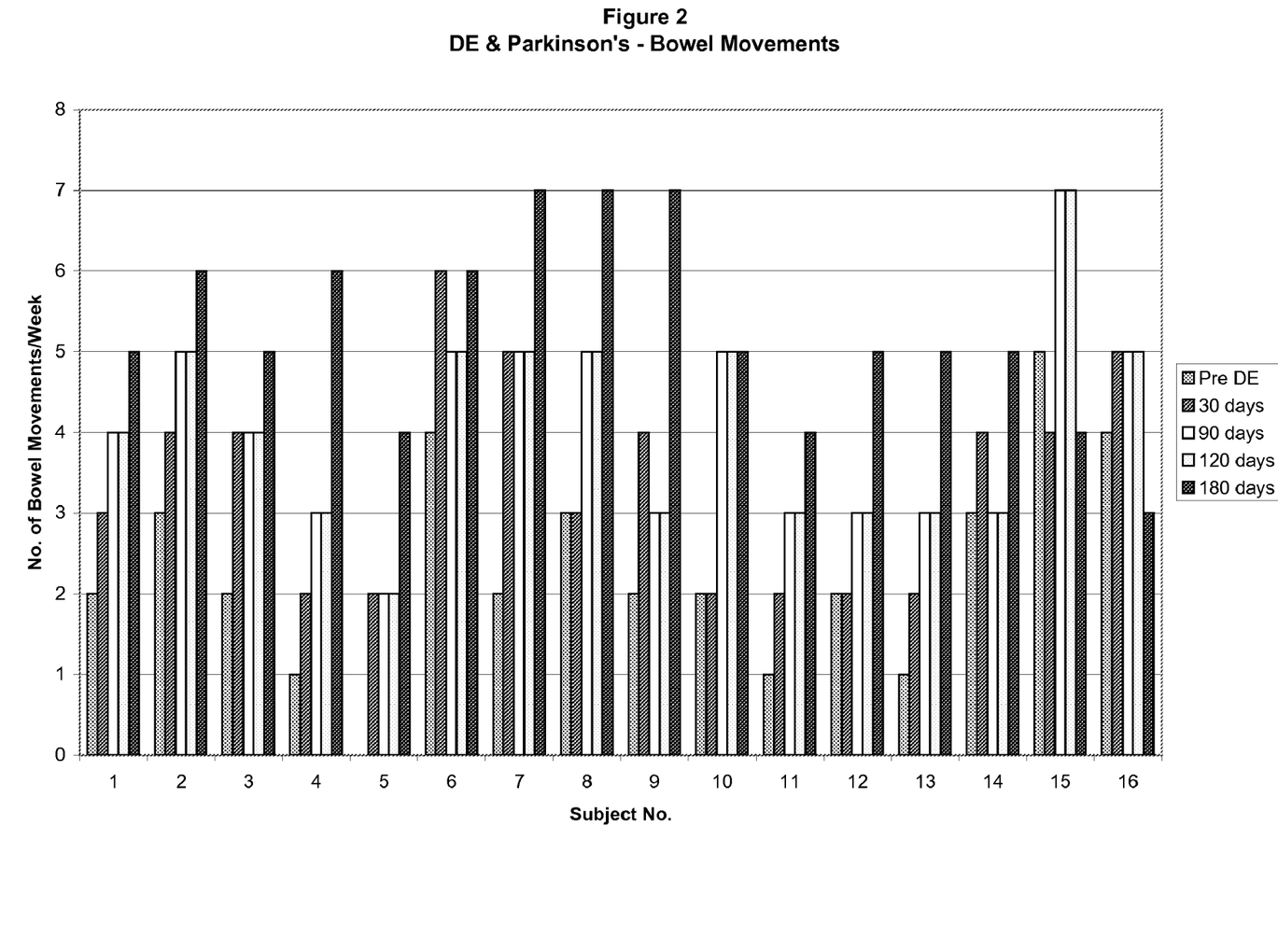
FIG. 2 is a graph demonstrating the increase in the number of bowel movements in Parkinson's patients after administration of digestive enzymes over a period of 180 days.

Referring to FIG. 2, the number of bowel movements per week experienced by most of the subjects was lower than normal prior to any treatment with digestive enzymes. The subjects were monitored at 30, 90, 120 and 180 day intervals. Over the course of the 180 day treatment, the number of bowel movements per week increased to 3 or more in the majority of subjects.

Static tremors, or "resting tremors", are tremors that occurs despite the limb being fully supported and at rest against gravity. They usually progress at the rate of 4-7 Hz (hertz), and are the typical Parkinsonian tremor. The amplitude of the tremor often decrease with sleep, complete relaxation or voluntary activity. Tremors are often the first symptom that people with Parkinson's disease or their family members notice. Initially, the tremors may appear in just one limb (arm or leg) or only on one side of the body. The tremors also may affect the lips, tongue, neck, or eyelids. As the disease progresses, the tremors may spread to both sides of the body, although in some cases the tremors remain on just one side. Emotional and physical stress tend to make the tremors worse.

Figure 3:
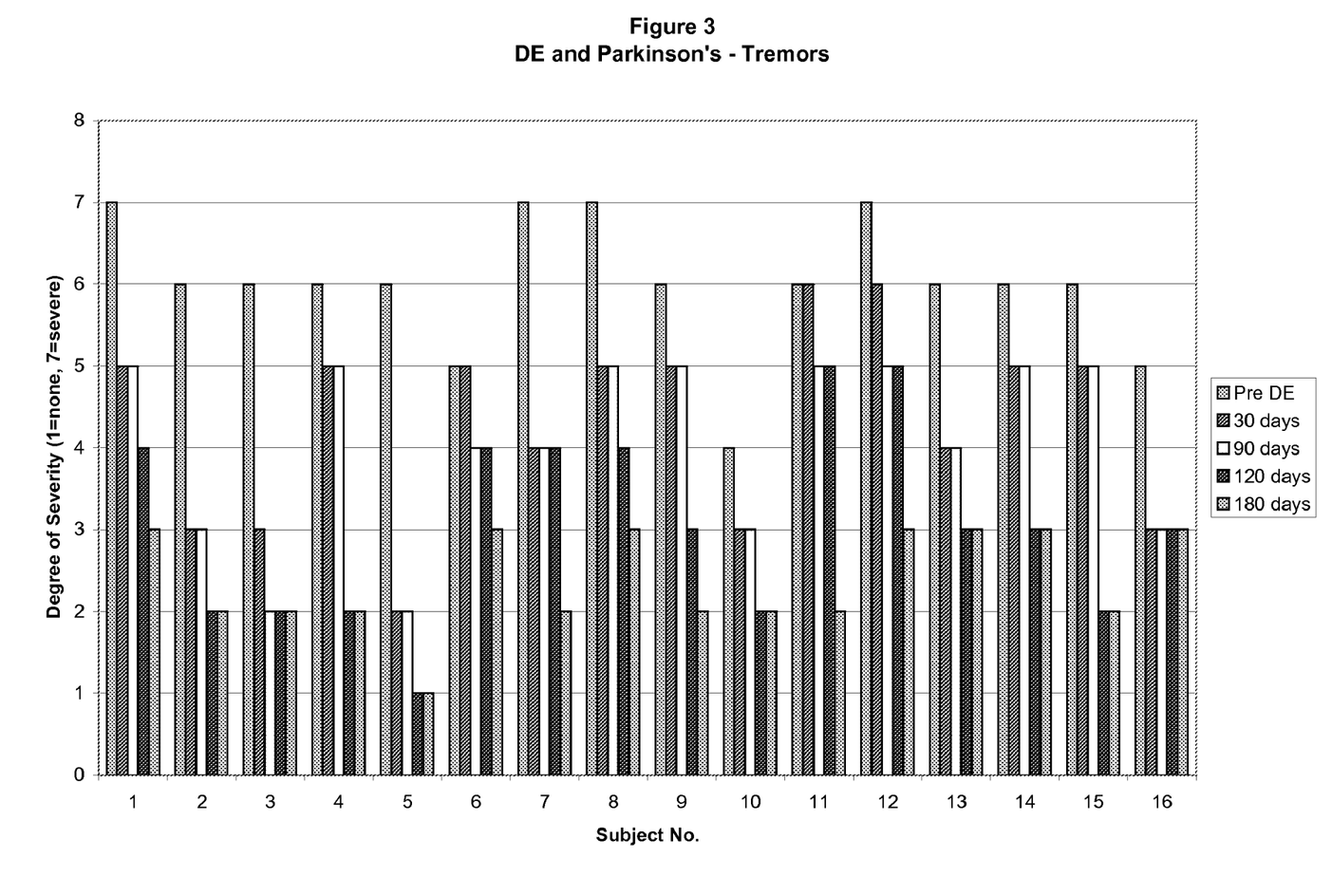
FIG. 3 is a graph demonstrating the decrease in occurrences of tremors in Parkinson's patients after administration of digestive enzymes over a period of 180 days.

Referring to FIG. 3, a majority of the subjects experienced severe tremors prior to any treatment with digestive enzymes. The severity of the tremors was measured on a scale of 1 to 7, with 1 equaling no tremors and 7 equaling severe tremors. The subjects were monitored at 30, 90, 120 and 180 day intervals. Over the course of the 180 day treatment, the severity of the tremors decreased from severe to moderate to mild in a majority of the subjects.

Many Parkinson's patients develop gait and balance problems and this can lead to falls. Ambulation is with a stooped posture using a short, shuffling gait. This is primarily due to the loss of balance control. Unfortunately with Parkinson's disease, the muscles become stiff and patients have difficulty swinging their arms when walking which helps in keeping one's balance. They also have episodes of freezing which literally have them "stuck in place" when initiating a step and they exhibit a slight foot drag which makes tripping easy. Persons with Parkinson's have difficulty in judging spatial relationships. Thus, falls often happen when navigating through doorways or through narrow passages.

Figure 4:
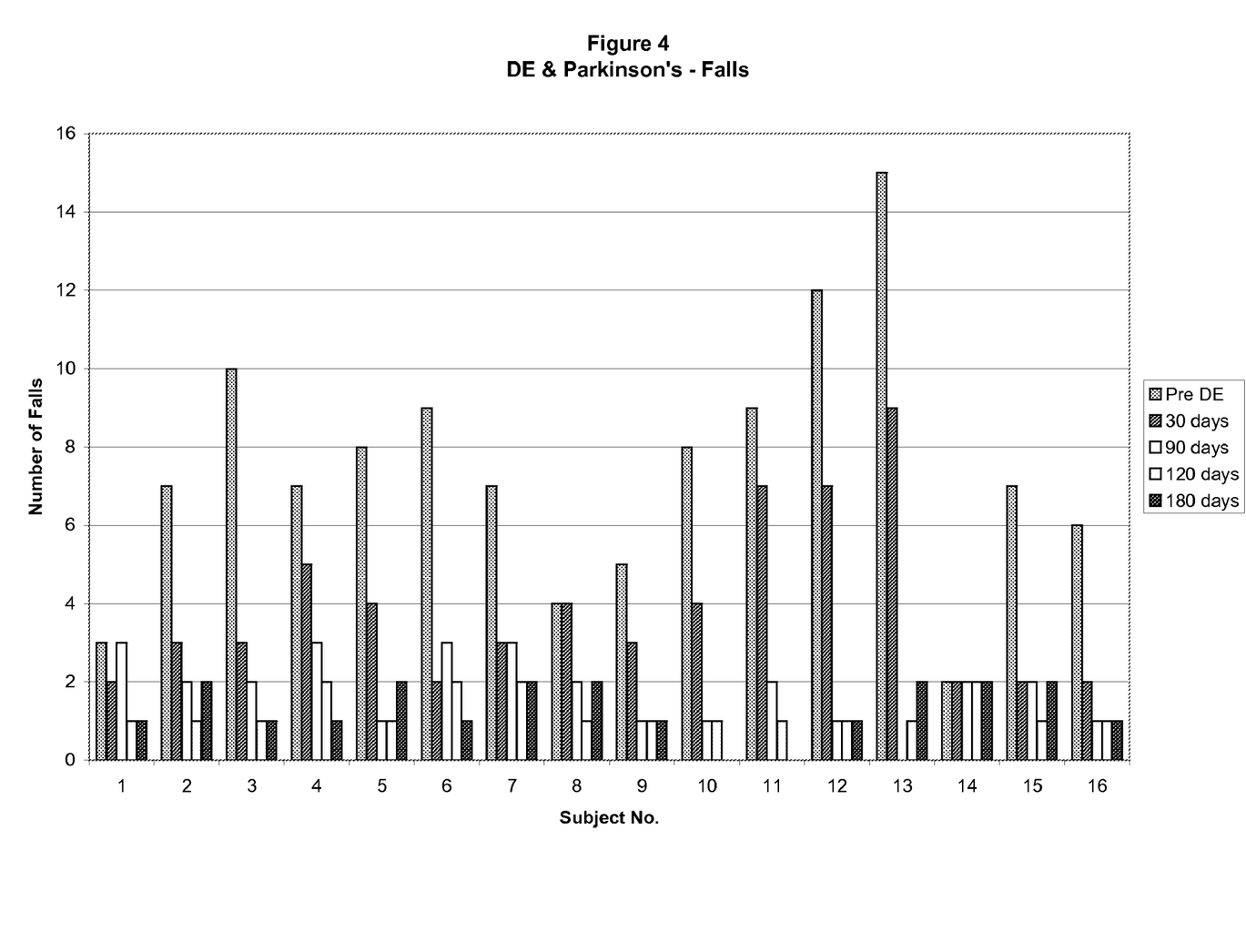
FIG. 4 is a graph demonstrating the decrease in occurrences of falls in Parkinson's patients after administration of digestive enzymes over a period of 180 days.

Referring to FIG. 4, a majority of the subjects experienced an elevated number of falls prior to any treatment with digestive enzymes. The subjects were monitored at 30, 90, 120 and 180 days. Over the course of the 180 day treatment, the number of falls decreased to less than two per week in a majority of the subjects.

Figure 5:
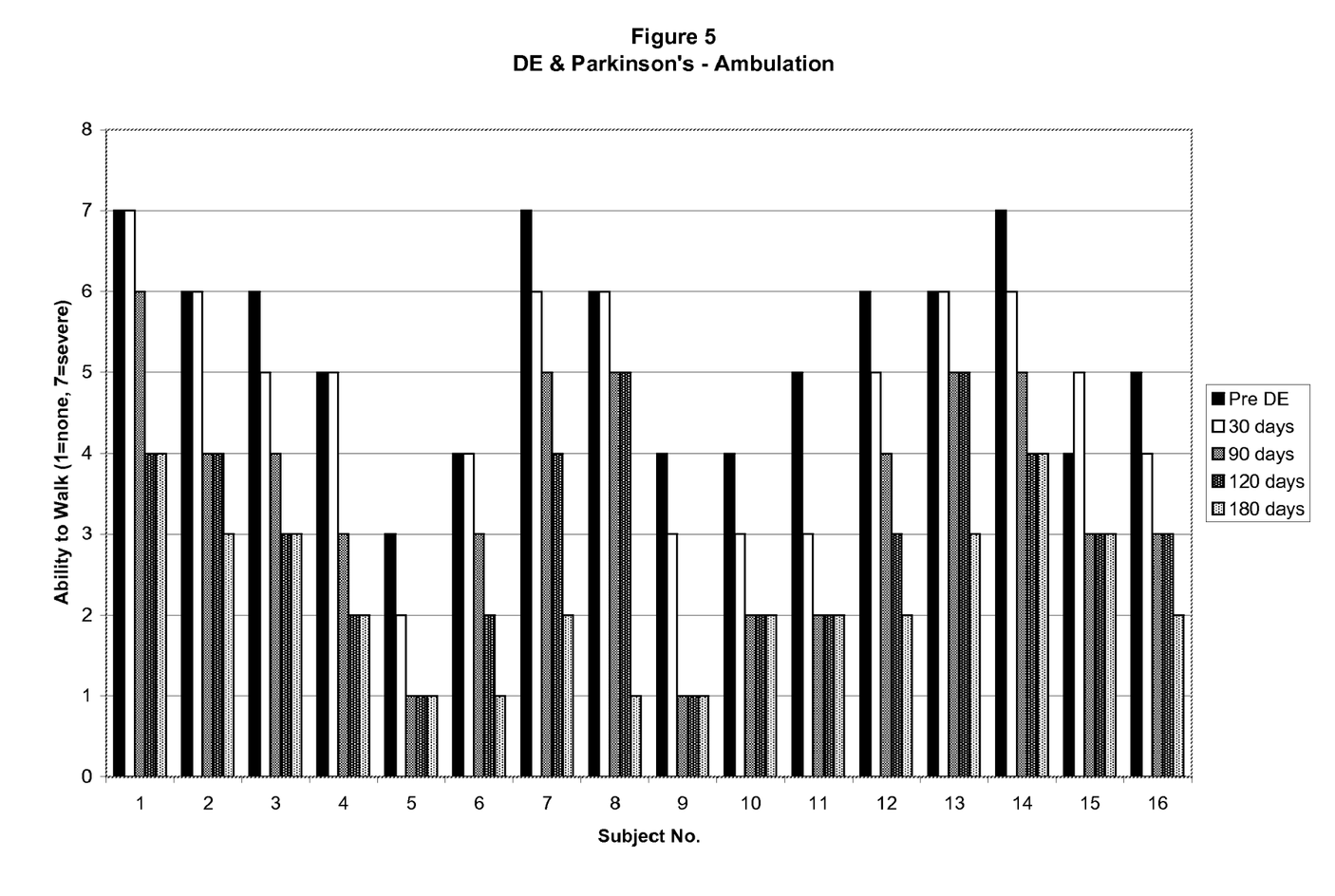
FIG. 5 is a graph demonstrating the changes in ambulation in Parkinson's patients after administration of digestive enzymes over a period of 180 days.

Referring to FIG. 5, a majority of the subjects experienced severe difficulty in ambulation prior to any treatment with digestive enzymes. The difficulty in ambulation was measured on a scale of 1 to 7, with 1 equaling no difficulty and 7 equaling severe difficulty. The subjects were monitored at 30, 90, 120 and 180 day intervals. Over the course of the 180 day treatment, the difficulty in ambulation decreased from severe to moderate to some or no difficulty in a majority of the subjects.

Fecal chymotrypsin levels were also measured in the 16 subjects and compared to the fecal chymotrypsin levels of 16 subjects who did not have Parkinson's disease. The non-Parkinson's subjects ranged in age from 44 to 77. Fecal chymotrypsin is a sensitive, specific measure of proteolytic activity. Normal levels of chymotrypsin are considered be greater than 8.4 U/gram. Decreased values (less than 4.2 U/gram) suggest diminished pancreatic output (pancreatic insufficiency), hypoacidity of the stomach or cystic fibrosis. Elevated chymotrypsin values suggest rapid transit time, or less likely, a large output of chymotrypsin from the pancreas.

A stool sample was collected from each of the subjects. Each stool sample was analyzed using an enzymatic photospectrometry analysis to determine the level of fecal chymotrypsin in the stool. Alternatively, other methods, such as the calorimetric method, use of substrates, use of assays, and/or any other suitable method may be used to measure the fecal chymotrypsin levels. The levels of fecal chymotrypsin in the Parkinson's patients was compared to the levels of fecal chymotrypsin in the non-Parkinson's subjects to determine if the Parkinson's patients would benefit from the administration of digestive enzymes.

Figure 6:
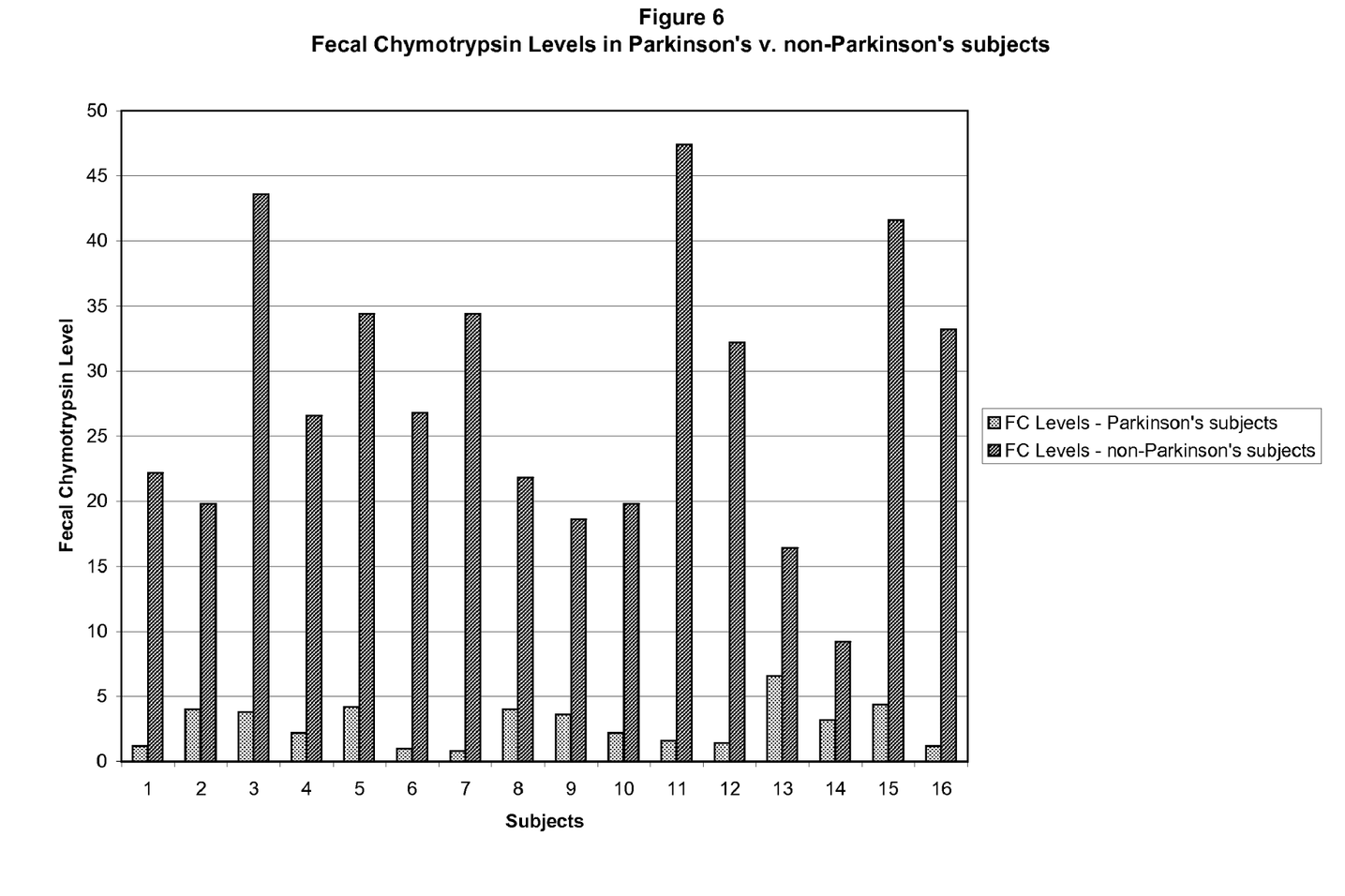
FIG. 6 is a graph demonstrating the difference in the fecal chymotrypsin levels of Parkinson's and non-Parkinson's subjects.

Referring to FIG. 6, the fecal chymotrypsin levels of the Parkinson's patients ranged from 0.8 to 6.6 U/gram, with a mean of 2.84 U/gram, while the fecal chymotrypsin levels of the non-Parkinson's patients ranged from 9.2. to 47.4 U/gram, with a mean of 28 U/gram. Thus, it can be seen that the fecal chymotrypsin levels of the Parkinson's patients were markedly decreased when compared to the non-Parkinson's subjects.

In summary, the results of the study described herein demonstrate that administration of digestive enzymes benefits individuals having a dysautonomic disorder, such as Parkinson's disease, by ameliorating the symptoms of the disorder. Furthermore, the results of the study indicate that measurement of the fecal chymotrypsin level in individuals having a dysautonomic disorder can determine if the individual will benefit from the administration of digestive enzymes.

The foregoing description of the embodiments of the invention has been presented for the purposes of illustration and description. It is not intended to be exhaustive or to limit the invention to the precise form disclosed. Many modifications and variations are possible in light of this disclosure. It is intended that the scope of the invention be limited not by this detailed description, but rather by the claims appended hereto.

What is claimed is:

1. A method of diagnosing a patient comprising:
   a. obtaining a fecal sample from the patient;
   b. determining a level of chymotrypsin present in the fecal sample; and
   c. diagnosing the patient as having a likelihood to develop a dysautonomic disorder if the determined fecal chymotrypsin level is 8.4 U/gram or less, wherein said dysautonomic disorder is selected from the group consisting of Familial dysautonomia (FD), Diabetic autonomic failure, Parkinson's disease or Orthostatic intolerance.

2. The method of claim 1, wherein the fecal chymotrypsin level is between 8.4 and 4.2 U/gram.

3. The method of claim 1, wherein the fecal chymotrypsin level is less than 4.2 U/gram.

4. The method of claim 1, wherein the level of chymotrypsin present in the fecal sample is determined using an enzymatic photospectrometry method.

5. The method of claim 1, further comprising determining if the patient exhibits one or more symptoms of a dysautonomic disorder.

6. The method of claim 1, wherein the patient exhibits one or more symptoms of a dysautonomic disorder.

7. The method of claim 1, wherein the level of chymotrypsin present in the fecal sample is determined at 30° C.

8. A method of screening a patient comprising:
   a. determining the level of chymotrypsin present in a fecal sample obtained from the patient; and
   b. identifying the patient as having a likelihood to develop a dysautonomic disorder if the determined chymotrypsin level is 8.4 U/gram or less, wherein said dysautonomic disorder is selected from the group consisting of Familial dysautonomia (FD), Diabetic autonomic failure, Parkinson's disease or Orthostatic intolerance.

9. The method of claim 8, wherein the level of chymotrypsin present in the fecal sample is determined using an enzymatic photospectrometry method.

10. The method of claim 8, further comprising determining if the patient exhibits one or more symptoms of a dysautonomic disorder.

11. The method of claim 8, wherein the level of chymotrypsin present in the fecal sample is determined at 30° C.

12. A method of confirming a diagnosis of a patient as having a dysautonomic disorder or a likelihood to develop a dysautonomic disorder, comprising:
   a. obtaining a fecal sample from the patient;
   b. determining a level of chymotrypsin present in the fecal sample; and
   c. confirming the diagnosis of the patient as having a dysautonomic disorder or a likelihood to develop a dysautonomic disorder if the determined fecal chymotrypsin level is 8.4 U/gram or less, wherein said dysautonomic disorder is selected from the group consisting of Familial dysautonomia (FD), Diabetic autonomic failure, Parkinson's disease or Orthostatic intolerance.

13. The method of claim 12, wherein the level of chymotrypsin present in the fecal sample is determined using an enzymatic photospectrometry method.

14. The method of claim 12, further comprising determining if the patient exhibits one or more symptoms of a dysautonomic disorder.

15. The method of claim 12, wherein the level of chymotrypsin present in the fecal sample is determined at 30° C.

16. A method of confirming a diagnosis of a patient as having a dysautonomic disorder or a likelihood to develop a dysautonomic disorder comprising:
   a. determining the level of chymotrypsin present in a fecal sample obtained from the patient; and
   b. confirming the diagnosis of the patient as having a dysautonomic disorder or a likelihood to develop a dysautonomic disorder if the determined chymotrypsin level is 8.4 U/gram or less, wherein said dysautonomic disorder is selected from the group consisting of Familial dysautonomia (FD), Diabetic autonomic failure, Parkinson's disease or Orthostatic intolerance.

17. The method of claim 16, wherein the level of chymotrypsin present in the fecal sample is determined using an enzymatic photospectrometry method.

18. The method of claim 16, further comprising determining if the patient exhibits one or more symptoms of a dysautonomic disorder.

19. The method of claim 16, wherein the level of chymotrypsin present in the fecal sample is determined at 30° C.

20. A method of determining if an individual has a likelihood propensity to develop a dysautonomic disorder comprising:
   a. determining the fecal chymotrypsin levels of the patient over a period of time; and
   b. determining that the individual has a likelihood to develop a dysautonomic disorder if the determined fecal chymotrypsin levels exhibit a decreasing trend over time and at least one level is 8.4 U/gram or less, wherein said dysautonomic disorder is selected from the group consisting of Familial dysautonomia (FD), Diabetic autonomic failure, Parkinson's disease or Orthostatic intolerance.

21. The method of claim 20, wherein the level of chymotrypsin present in the fecal sample is determined using an enzymatic photospectrometry method.

22. The method of claim 20, further comprising determining if the patient exhibits one or more symptoms of a dysautonomic disorder.

23. The method of claim 20, wherein the level of chymotrypsin present in the fecal sample is determined at 30° C.

24. A method of diagnosing a patient comprising:
   a. determining a level of chymotrypsin present in a fecal sample obtained from the patient; and
   b. diagnosing the patient as having a dysautonomic disorder or having a likelihood to develop a dysautonomic disorder if the determined fecal chymotrypsin level is less than a normal fecal chymotrypsin level, wherein said dysautonomic disorder is selected from the group consisting of Familial dysautonomia (FD), Diabetic autonomic failure, Parkinson's disease or Orthostatic intolerance.

25. The method of claim 24, wherein the level of chymotrypsin present in the fecal sample is determined at 30° C.

26. The method of claim 24, wherein the normal fecal chymotrypsin level is a level of fecal chymotrypsin associated with at least one other individual of the same approximate age that does not have the disorder.

27. The method of claim 24, further comprising determining if the patient exhibits one or more symptoms of a dysautonomic disorder.

28. A method of screening a patient comprising:
   a. determining a level of chymotrypsin present in a fecal sample obtained from the patient; and
   b. identifying the patient as having a likelihood to develop a dysautonomic disorder if the determined fecal chymotrypsin level is less than a threshold fecal chymotrypsin level, wherein said dysautonomic disorder is selected from the group consisting of Familial dvsautonomia (FD), Diabetic autonomic failure, Parkinson's disease or Orthostatic intolerance.

29. The method of claim 28, wherein the level of chymotrypsin present in the fecal sample is determined at 30° C.

30. The method of claim 28, further comprising determining if the patient exhibits one or more symptoms of a dysautonomic disorder.

31. A method of confirming a diagnosis of a patient as having a dysautonomic disorder or having a likelihood to develop a dysautonomic disorder, comprising:
   a. determining a level of chymotrypsin present in a fecal sample obtained from the patient; and
   b. confirming the diagnosis of the patient as having a dysautonomic disorder or having a likelihood to develop a dysautonomic disorder if the determined fecal chymotrypsin level is less than a normal fecal chymotrypsin level, wherein said dysautonomic disorder is selected from the group consisting of Familial dysautonomia (FD), Diabetic autonomic failure, Parkinson's disease or Orthostatic intolerance.

32. The method of claim 31, wherein the level of chymotrypsin present in the fecal sample is determined at 30° C.

33. The method of claim 31, wherein the normal fecal chymotrypsin level is a level of fecal chymotrypsin associated with at least one other individual of the same approximate age that does not have the disorder.

34. The method of claim 31, further comprising determining if the patient exhibits one or more symptoms of a dysautonomic disorder.

35. A method of confirming a diagnosis of a patient as having a dysautonomic disorder or having a likelihood to develop a dysautonomic disorder, comprising:
   a. determining a level of chymotrypsin present in a fecal sample obtained from the patient; and
   b. confirming the diagnosis of the patient as having a dysautonomic disorder or having a likelihood to develop a dysautonomic disorder if the determined fecal chymotrypsin level is less than a threshold fecal chymotrypsin level, wherein said dysautonomic disorder is selected from the group consisting of Familial dysautonomia (FD), Diabetic autonomic failure, Parkinson's disease or Orthostatic intolerance.

36. The method of claim 35, wherein the level of chymotrypsin present in the fecal sample is determined at 30° C.

37. The method of claim 35, further comprising determining if the patient exhibits one or more symptoms of a dysautonomic disorder.

38. The method of claim 1, 12, 16, 20, 24, 28, 31 or 35 herein the dysautonomic disorder is Parkinson's disease.

39. The method of claim 1, 12, 16, 20, 24, 28, 31 or 35 wherein the dysautonomic disorder is Familial dysautonomia (FD).

40. The method of claim 1, 12, 16, 20, 24, 28, 31 or 35 wherein the dysautonomic disorder is Diabetic autonomic failure.

41. The method of claim 1, 12, 16, 20, 24, 28, 31 or 35 wherein the dysautonomic disorder is Orthostatic intolerance.

* * * * *

UNITED STATES PATENT AND TRADEMARK OFFICE
CERTIFICATE OF CORRECTION

| | | |
|---|---|---|
| PATENT NO. | : 8,012,710 B2 | Page 1 of 1 |
| APPLICATION NO. | : 12/487868 | |
| DATED | : September 6, 2011 | |
| INVENTOR(S) | : Joan M. Fallon | |

It is certified that error appears in the above-identified patent and that said Letters Patent is hereby corrected as shown below:

In Column 10, Line 42, Claim 20; cancel "20. A method of determining if an individual has a likelihood propensity to develop a dystauonomic disorder comprising:" and insert the following:

--20. A method of determining if an individual has a likelihood to develop a dystauonomic disorder comprising:--

In Column 11, Line 24, Claim 28; "dvsautonomia" should be replaced with --dystauonomia--

In Column 12, Line 30, Claim 38; "claim" should be replaced with --claims--
In Column 12, Line 31, Claim 38; "herein" should be replaced with --wherein--
In Column 12, Line 32, Claim 39; "claim" should be replaced with --claims--
In Column 12, Line 35, Claim 40; "claim" should be replaced with --claims--

Signed and Sealed this
Twenty-fifth Day of October, 2011

David J. Kappos
*Director of the United States Patent and Trademark Office*